United States Patent
Olsen

(10) Patent No.: US 7,201,746 B2
(45) Date of Patent: Apr. 10, 2007

(54) IMPLANTABLE THERAPEUTIC SUBSTANCE DELIVERY DEVICE HAVING A PISTON PUMP WITH AN ANTI-CAVITATION VALVE

(75) Inventor: James M. Olsen, Plymouth, MN (US)

(73) Assignee: Medtronic, Inc., Minneapolis, MN (US)

(*) Notice: Subject to any disclaimer, the term of this patent is extended or adjusted under 35 U.S.C. 154(b) by 36 days.

(21) Appl. No.: 09/952,870

(22) Filed: Sep. 14, 2001

(65) Prior Publication Data

US 2002/0173772 A1 Nov. 21, 2002

Related U.S. Application Data

(60) Provisional application No. 60/282,777, filed on Apr. 10, 2001.

(51) Int. Cl.
*A61K 9/22* (2006.01)

(52) U.S. Cl. .................. 604/891.1; 604/288.01

(58) Field of Classification Search ............. 604/151, 604/152, 246, 247, 891.1, 288.01, 288.03, 604/288.04

See application file for complete search history.

(56) References Cited

U.S. PATENT DOCUMENTS

| 3,846,682 | A | | 11/1974 | Massie |
| 4,071,042 | A | | 1/1978 | Lombard et al. |
| 4,102,610 | A | | 7/1978 | Taboada et al. |
| 4,210,409 | A | | 7/1980 | Child |
| 4,265,241 | A | * | 5/1981 | Portner et al. .......... 604/131 |
| 4,360,019 | A | * | 11/1982 | Portner et al. .......... 604/131 |
| 4,437,815 | A | * | 3/1984 | McMullen ............... 604/152 |
| 4,487,603 | A | * | 12/1984 | Harris ..................... 604/152 |
| 4,525,165 | A | * | 6/1985 | Fischell .................. 604/131 |
| 4,541,787 | A | | 9/1985 | DeLong |

(Continued)

FOREIGN PATENT DOCUMENTS

CH 657275 8/1986

(Continued)

OTHER PUBLICATIONS

"Valves, Piping & Piplines Handbook", *Elsevier Advanced Technology*, XP-002200965, Chapter entitled "Cavitation", pp. 658-666.
Brochure, "SynchroMed® Infusion System", 4 pgs., (1995).

*Primary Examiner*—Nicholas D. Lucchesi
*Assistant Examiner*—Matthew DeSanto
(74) *Attorney, Agent, or Firm*—Mueting, Raasch & Gebhardt, P.A.

(57) ABSTRACT

A medical device known as an implantable therapeutic substance infusion device is configured for implanting in humans to deliver a therapeutic substance such as pharmaceutical compositions, genetic materials, and biologics to treat a variety of medical conditions such as pain, spastisity, cancer, and many other conditions. The therapeutic substance infusion device has a piston pump with an anti-cavitation valve to reduce gas formation, increase accuracy, improve efficiency and has many other improvements. The therapeutic substance infusion device has a housing, a therapeutic substance reservoir, a power source carried in the housing, electronics, a piston pump, an inlet valve, and anti-cavitation valve. The piston pump is configured for pumping therapeutic substance from the therapeutic substance reservoir through an infusion port at a programmed rate. The anti-cavitation is in fluid communication with a reservoir outlet and an inlet chamber to substantially preventing retrograde flow of therapeutic substance from the inlet chamber back through the reservoir outlet. Many embodiments of the anti-cavitation valve and its methods of operation are possible.

48 Claims, 18 Drawing Sheets

U.S. PATENT DOCUMENTS

| | | | |
|---|---|---|---|
| 4,568,250 A | 2/1986 | Falk et al. | |
| 4,569,641 A | 2/1986 | Falk et al. | |
| 4,596,575 A * | 6/1986 | Rosenberg et al. | 604/891.1 |
| 4,636,150 A | 1/1987 | Falk et al. | |
| 4,690,371 A | 9/1987 | Bosley et al. | |
| 4,714,462 A * | 12/1987 | DiDomenico | 604/67 |
| 4,714,762 A | 12/1987 | DiDomenico | |
| 4,775,301 A | 10/1988 | Cartwright et al. | |
| 4,883,467 A | 11/1989 | Franetzki et al. | |
| 4,965,864 A | 10/1990 | Roth et al. | |
| 4,985,015 A | 1/1991 | Obermann et al. | |
| 5,085,563 A | 2/1992 | Collins et al. | |
| 5,318,521 A | 6/1994 | Slettenmark | |
| 5,434,549 A | 7/1995 | Hirabayashi et al. | |
| 5,462,525 A | 10/1995 | Srisathapat et al. | |
| 5,472,323 A * | 12/1995 | Hirabayashi et al. | 417/417 |
| 5,509,792 A | 4/1996 | Sullivan et al. | |
| 5,707,361 A | 1/1998 | Slettenmark | |
| 5,758,666 A | 6/1998 | Larson, Jr. et al. | |
| 5,797,733 A | 8/1998 | Falk et al. | |
| 5,833,440 A | 11/1998 | Berling | |
| 5,915,929 A | 6/1999 | Falk et al. | |
| 5,921,526 A | 7/1999 | Najmolhoda | |
| 5,947,155 A | 9/1999 | Miki et al. | |

FOREIGN PATENT DOCUMENTS

| | | |
|---|---|---|
| EP | 0605903 | 6/1997 |
| EP | 0 791 369 A | 8/1997 |
| JP | 55-142981 | 11/1980 |

* cited by examiner

IMPLANTABLE THERAPEUTIC SUBSTANCE DELIVERY DEVICE HAVING A PISTON PUMP WITH AN ANTI-CAVITATION VALVE

RELATED APPLICATIONS

This application claims the benefit of provisional application U.S. Ser. No. 60/282,777, filed Apr. 10, 2001, entitled "IMPLANTABLE THERAPEUTIC SUBSTANCE DELIVERY DEVICE HAVING A PISTON PUMP WITH AN ANTI-CAVITATION VALVE", by James M. Olsen.

This disclosure is related to the following copending applications entitled "PERMANENT MAGNET SOLENOID PUMP FOR AN IMPLANTABLE THERAPEUTIC SUBSTANCE DELIVERY DEVICE" by inventor Olsen (Application No. 60/282,775; filed Apr. 10, 2001) and "LOW PROFILE INLET VALVE FOR A PISTON PUMP THERAPEUTIC SUBSTANCE DELIVERY DEVICE" by inventor Olsen (Application No. 60/282,778; filed Apr. 10, 2001) which are not admitted as prior art with respect to the present disclosure by its mention in this section.

BACKGROUND OF THE INVENTION

This disclosure relates to a medical device and more particularly to an implantable therapeutic substance delivery device with a piston-operated pump.

The medical device industry produces a wide variety of electronic and mechanical devices for treating patient medical conditions such as pacemakers, defribulators, neurostimulators, and therapeutic substance delivery pumps. Medical devices can be configured to be surgically implanted or connected externally to the patient receiving treatment. Clinicians use medical devices alone or in combination with therapeutic substance therapies and surgery to treat patient medical conditions. For some medical conditions, medical devices provide the best, and sometimes the only, therapy to restore an individual to a more healthful condition and a fuller life. Implantable drug delivery pumps can be used to treat conditions such as pain, spasticity, cancer, and a wide variety of other medical conditions.

An implantable drug delivery pump is implanted by a clinician into a patient at a location appropriate for the therapy that interferes as little as practicable with patient activity such as subcutaneous in the lower abdomen. Typically, a drug delivery catheter is connected to the drug pump outlet and implanted to infuse the drug, infusate or other therapeutic substance at a programmed infusion rate and predetermined location to treat the medical condition. Reliable and accurate operation of the drug pump is important because both inadequate and unintended therapeutic substance delivery can create patient complications. Many drug pumps are configured, so the pump can be replenished with drug through a refill port or septum while the pump is implanted, so the period the pump can be implanted may not be limited by drug capacity. In electrically powered implantable drug pumps, the period the pump can be implanted is often limited by factors such as battery consumption, corrosive damage, and mechanical wear. The relative large size of some implantable drug pumps can limit locations where the device can be implanted in a patient. An example of an implantable drug pump is shown in Medtronic, Inc. "SynchroMed® Infusion System" Product Brochure (1995). Implantable drug pumps can use a variety of pumping mechanism such as a piston pump, rotary vane pump, osmotic pump, Micro Electro Mechanical Systems (MEMS) pump, diaphragm pump, peristaltic pump, and solenoid piston pump to infuse a drug into a patient.

Piston pumps such as variable reluctance piston pumps and piston pumps operate by applying an electromagnetic force to a pump piston. The electromagnetic force imparts movement to the pump piston to pump fluid from a pumping chamber into an outlet. Although the fluid flowing into a pumping chamber is controlled with a flow restrictor or an inlet valve, the fluid flowing into an inlet chamber is not typically controlled. Without a control such as valve on fluid flowing into the inlet chamber, fluid in the inlet chamber can backflow when the inlet chamber fluid is compressed to fill the pumping chamber. Backflow of fluid from the inlet chamber can cause low pumping chamber pressures that when the pumping chamber is being filled with fluid that in turn can cause gasses to come out of solution in the fluid. Additionally backflow of fluid out of the inlet chamber causes pump operation to be less efficient because fluid is being moved in and out of the inlet chamber for no operating purpose. An example of a previous piston pump with an inlet flow restrictor is shown in U.S. Pat. No. 4,883,467 "Reciprocating Pump For An Implantable Medication Dosing Device" by Franetzki et al. (Nov. 28, 1989), and an example of a previous piston pump inlet valve is shown in U.S. Pat. No. 4,636,150 "Low Power Electromagnetic Pump" by Falk et al. (Jan. 13, 1987).

For the foregoing reasons, there is a need for an anti-cavitation valve for a piston pump therapeutic substance delivery device that reduces gas formation, increases accuracy, improves efficiency and has many other improvements.

SUMMARY OF THE INVENTION

An anti-cavitation valve for a piston pump implantable therapeutic substance delivery device embodiment reduces gas formation, increases accuracy, improves efficiency, and has many other improvements. The anti-cavitation valve is in fluid communication with a reservoir outlet and an inlet chamber to substantially prevent retrograde flow of therapeutic substance from the inlet chamber back toward the reservoir outlet. The piston pump is coupled to electronics and coupled to a therapeutic substance reservoir outlet to pump therapeutic substance from the therapeutic substance reservoir through an infusion outlet at a programmed rate. The piston pump is carried in a therapeutic substance delivery device that has a housing, a therapeutic substance reservoir coupled to the housing, a power source carried in the housing, and electronics carried in the housing and coupled to the power source. Many embodiments of the anti-cavitation valve for a piston pump implantable therapeutic substance delivery device and its methods of operation are possible.

DETAILED DESCRIPTION OF THE PREFERRED EMBODIMENTS

Figure 1:
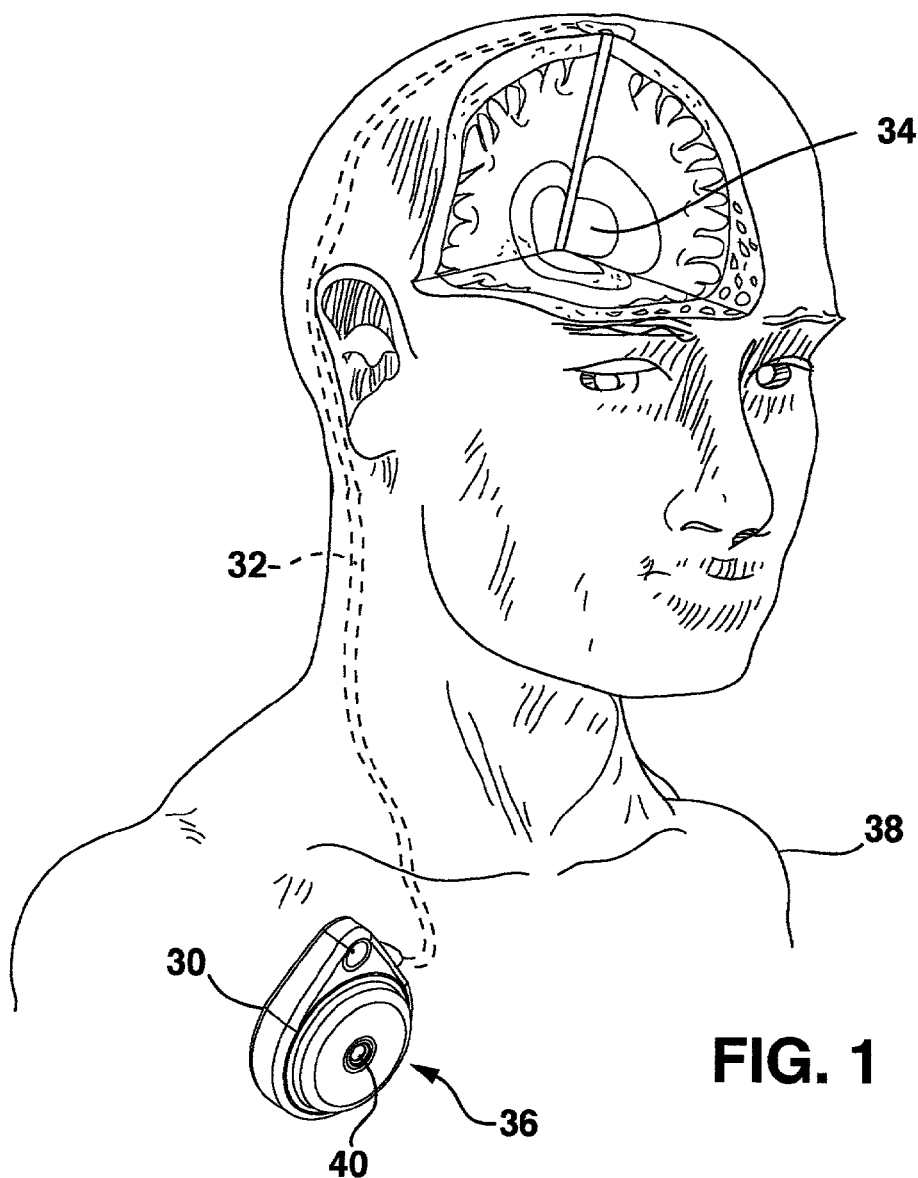
FIG. 1 shows the environment of an implantable therapeutic substance delivery device embodiment.
Figure 2:
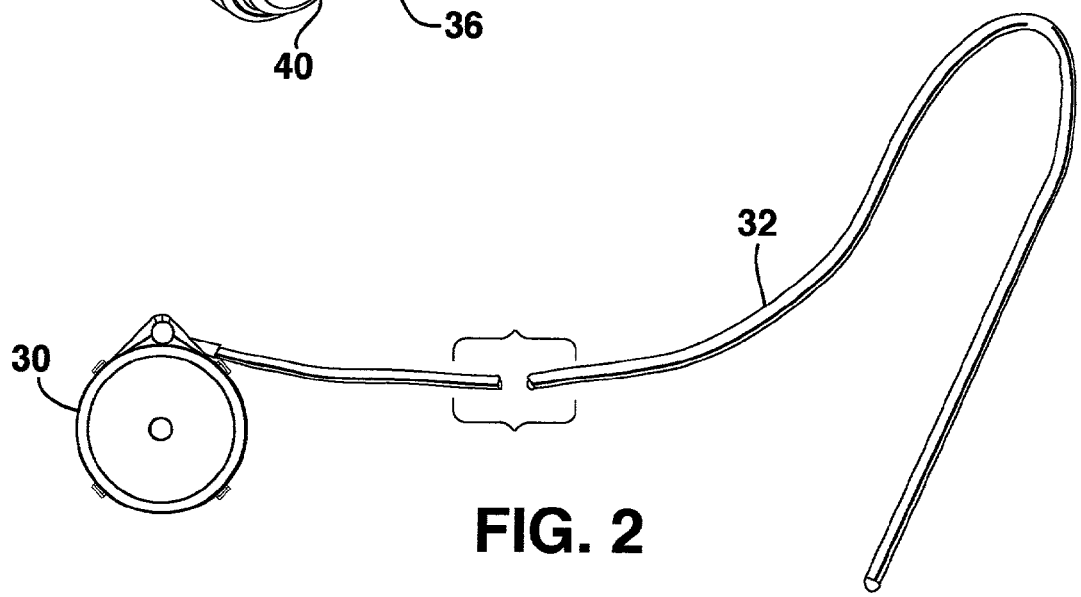
FIG. 2 shows an implantable therapeutic substance delivery device with catheter embodiment.

FIG. 1 shows the environment of an implantable medical device known as an implantable therapeutic substance delivery device 30, also known as a drug pump, having a piston pump embodiment. The therapeutic substance delivery device 30 can be used for a wide variety of therapies such as pain, spasticity, cancer, and many other medical conditions. The implantable therapeutic substance delivery device 30 is typically implanted by a clinician such as a surgeon in a sterile surgical procedure performed under local, regional, or general anesthesia. Before implanting the therapeutic substance delivery device 30, a catheter 32 is typically implanted with the distal end position at the desired therapeutic substance delivery site 34 and the proximal end tunneled to the location where the therapeutic substance delivery device 30 is to be implanted. The catheter 32 and the therapeutic substance delivery site 34 can generate a back pressure during infusion known as the infusion site pressure that the therapeutic substance delivery device 30 overcomes to deliver therapeutic substance 36 at the infusion site. The implantable therapeutic substance delivery device 30 is generally implanted subcutaneously about 2.5 cm (1.0 inch) beneath the skin where there is sufficient subcutaneous tissue to support the implanted system. Once the therapeutic substance delivery device 30 is subcutaneously implanted into the patent, the incision can be sutured closed and the therapeutic substance delivery device 30 can begin operation.

The therapeutic substance delivery device 30 operates to infuse a therapeutic substance 36 at a programmed rate into a patient 38. The therapeutic substance 36 is a product or substance intended to have a therapeutic effect such as pharmaceutical compositions, genetic materials, biologics, and other substances. Pharmaceutical compositions are chemical formulations intended to have a therapeutic effect such as intrathecal antispasmodics, pain medications, chemotherapeutic agents, and the like. Pharmaceutical compositions are often configured to function in an implanted environment with characteristics such as stability at body temperature to retain therapeutic qualities, concentration to reduce the frequency of replenishment, and the like. Genetic materials are substances intended to have a direct or indirect genetic therapeutic effect such as genetic vectors, genetic regulator elements, genetic structural elements, DNA, and the like. Biologics are substances that are living matter or derived from living matter intended to have a therapeutic effect such as stem cells, platelets, hormones, biologically produced chemicals, and the like. Other substances are substances intended to have a therapeutic effect yet are not easily classified such as saline solution, fluoroscopy agents, and the like.

The therapeutic substance 36 can be replenished in some embodiments of the implanted therapeutic substance delivery device 30 by inserting a non-coring needle connected to a syringe filled with therapeutic substance 36 through the patient's skin into a septum 40 on the therapeutic substance delivery device 30 to fill the implanted device. If the therapeutic substance delivery device 30 requires replacement due to conditions such as battery depletion or other condition, an incision is made near the implanted therapeutic substance delivery device 30, and the old therapeutic substance delivery device 30 is removed, also known as explanted. After the old therapeutic substance delivery device 30 has been explanted, typically a new therapeutic substance delivery device 30 is then implanted.

Figure 3:
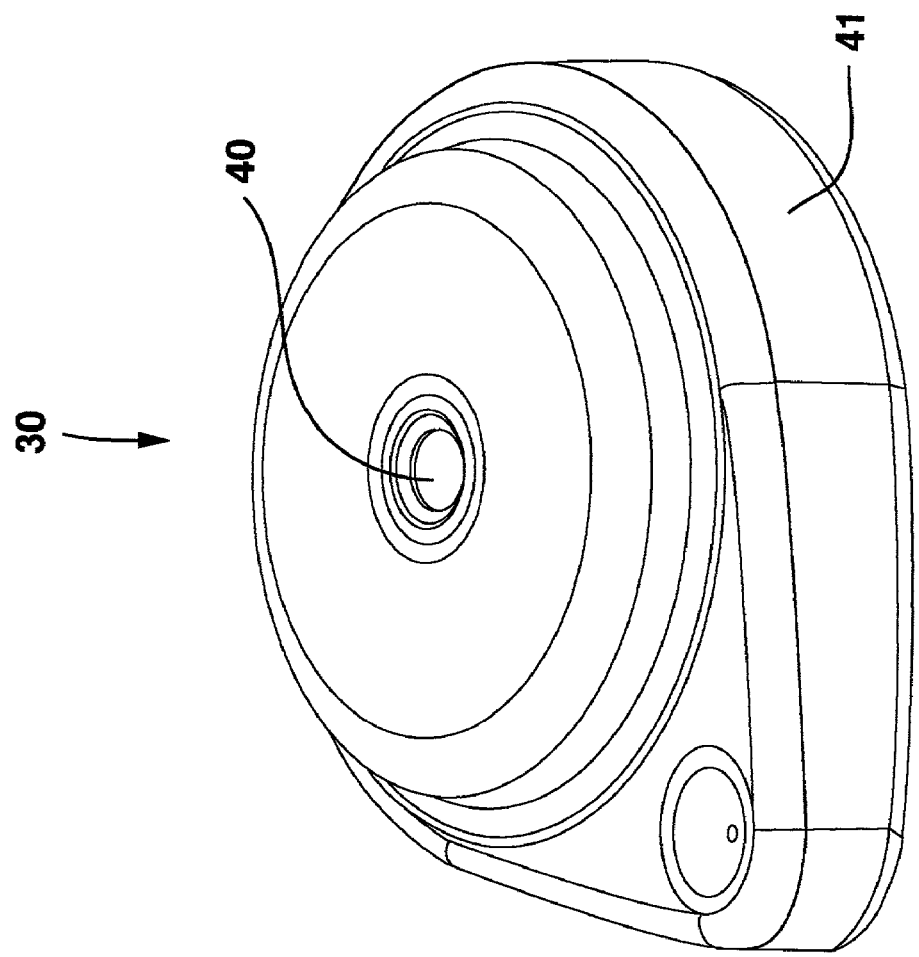
FIG. 3 shows an implantable therapeutic substance delivery device embodiment.
Figure 4:
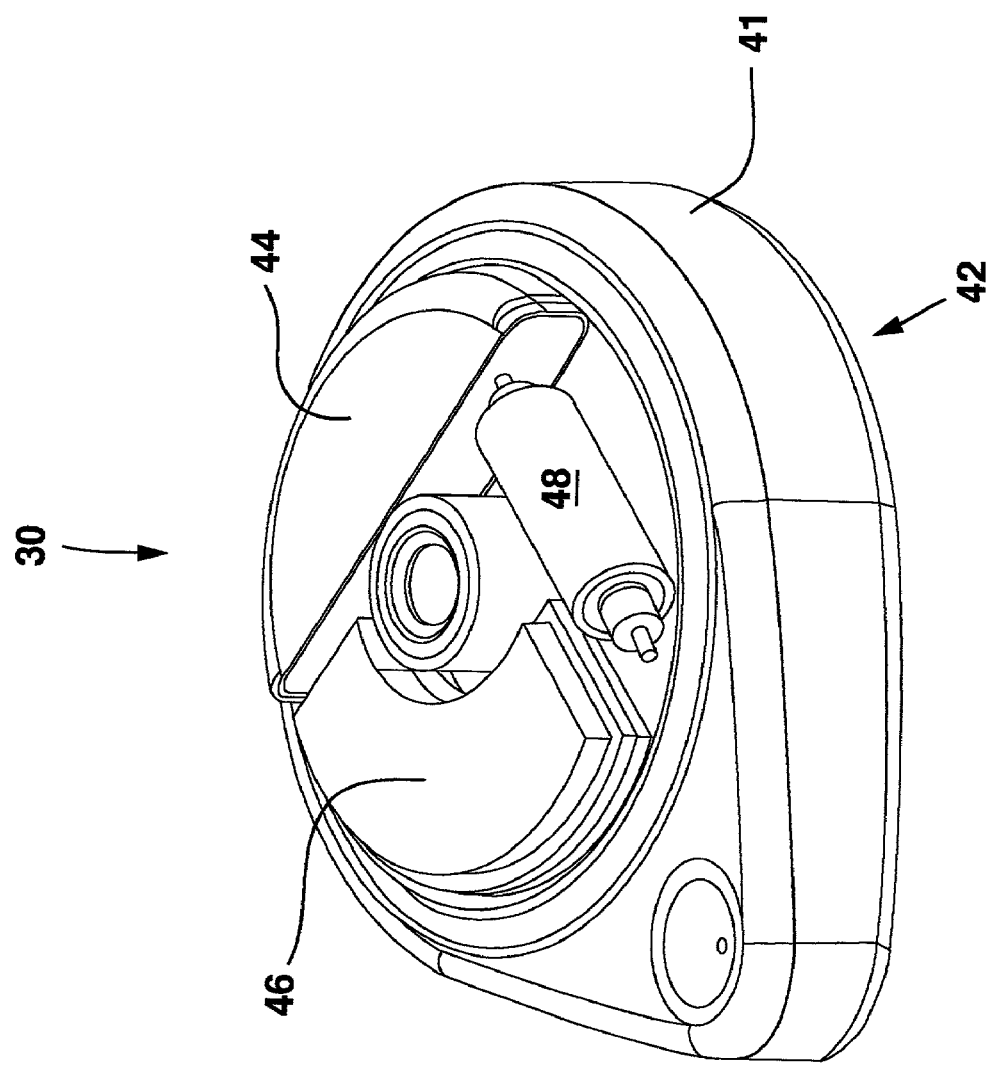
FIG. 4 shows the implantable therapeutic substance delivery device of FIG. 3 with a portion of a housing removed.
Figure 5:
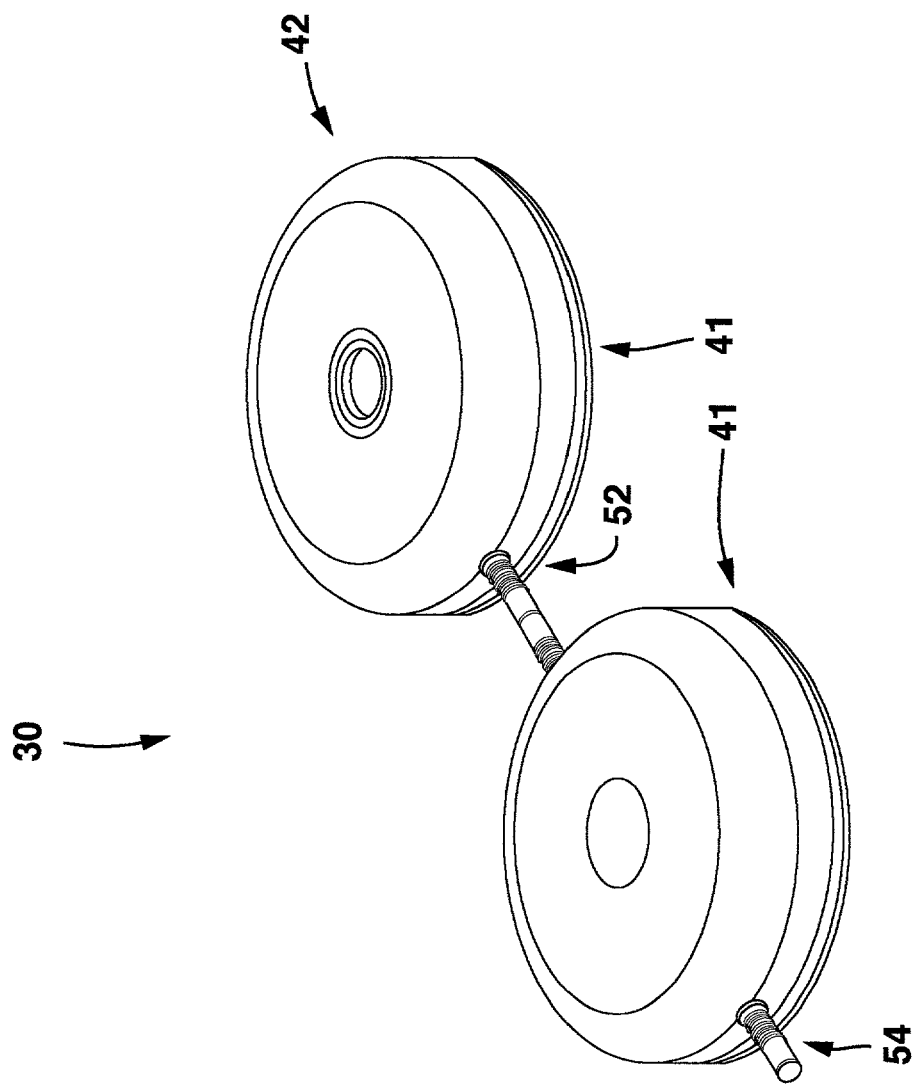
FIG. 5 shows another implantable therapeutic substance delivery device embodiment having a separate therapeutic substance reservoir.
Figure 6:
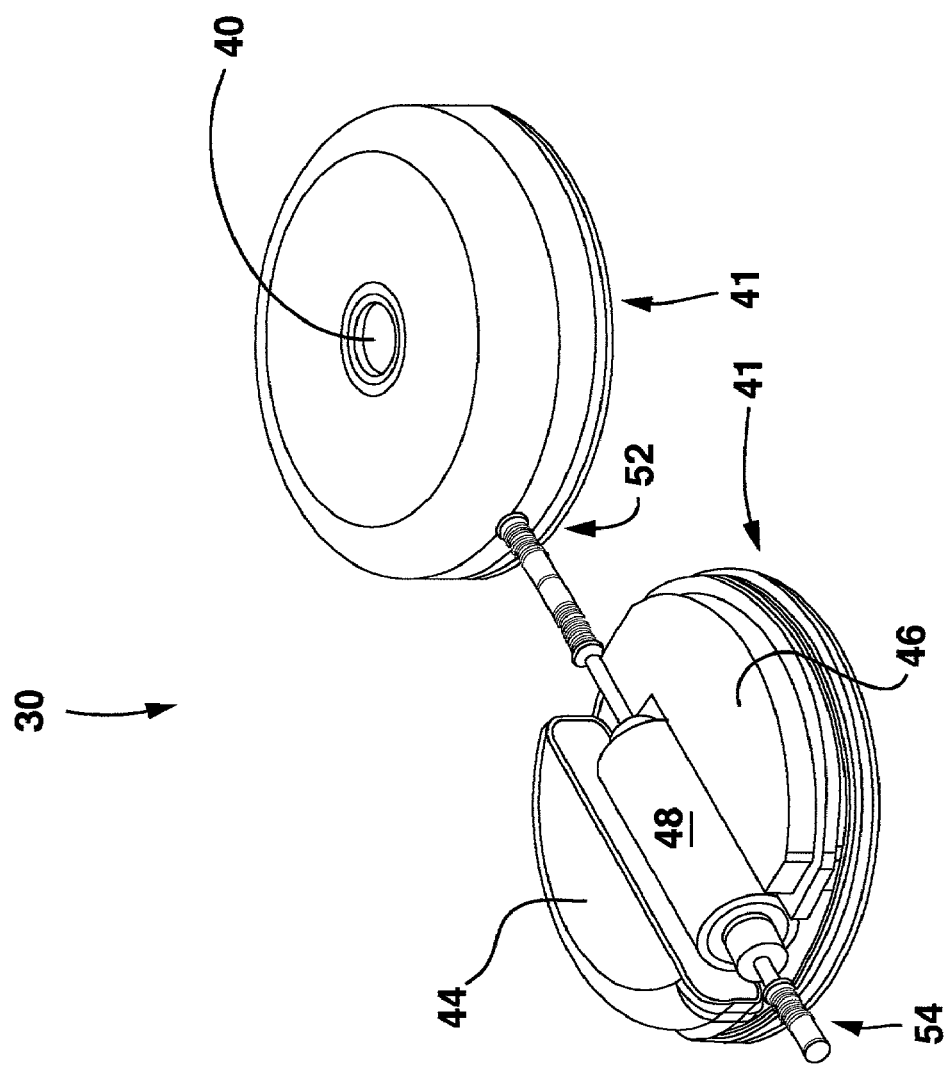
FIG. 6 shows the implantable therapeutic substance delivery device of FIG. 5 with a portion of a housing removed.
Figure 7:
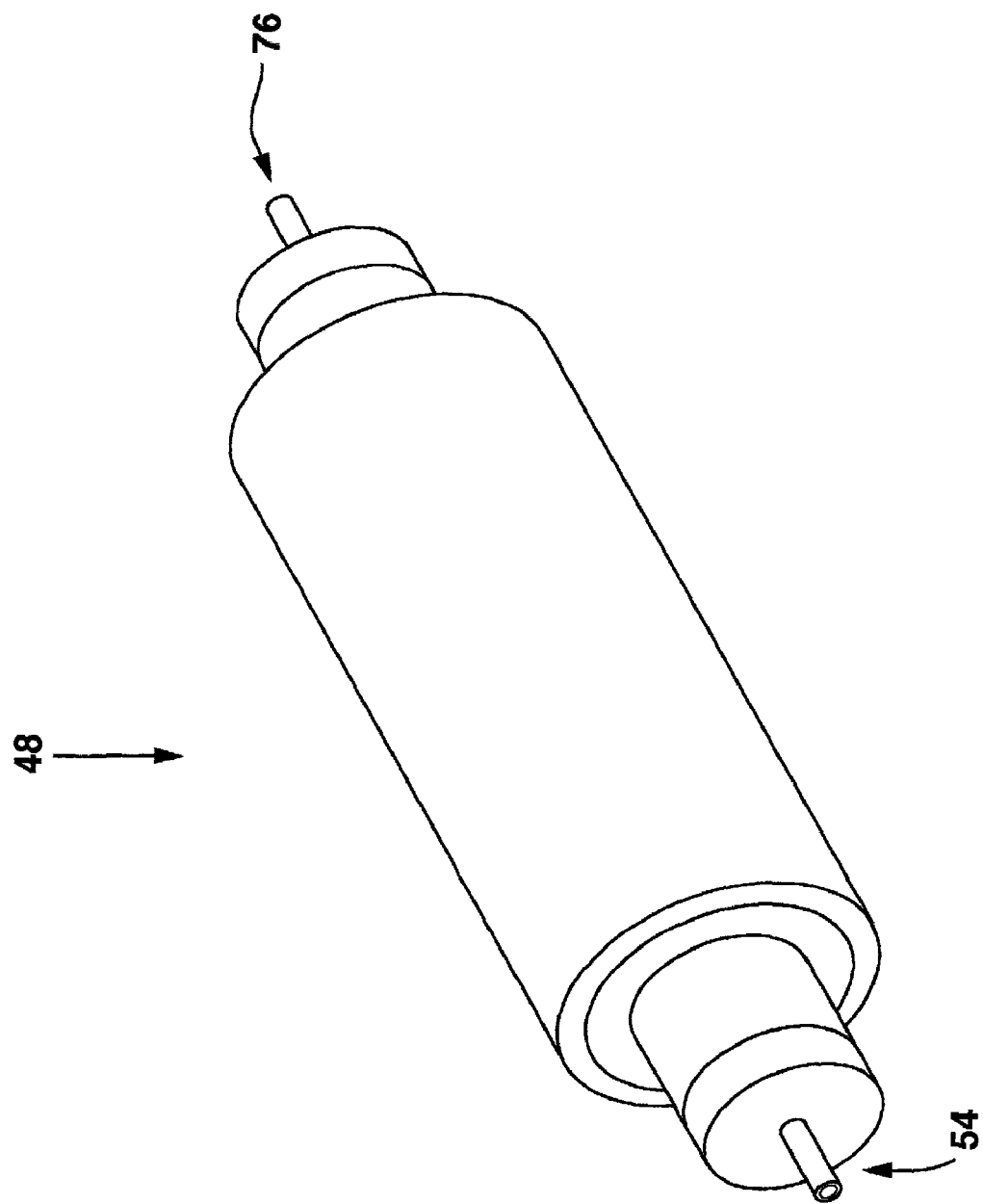
FIG. 7 shows a piston pump embodiment.
Figure 8:
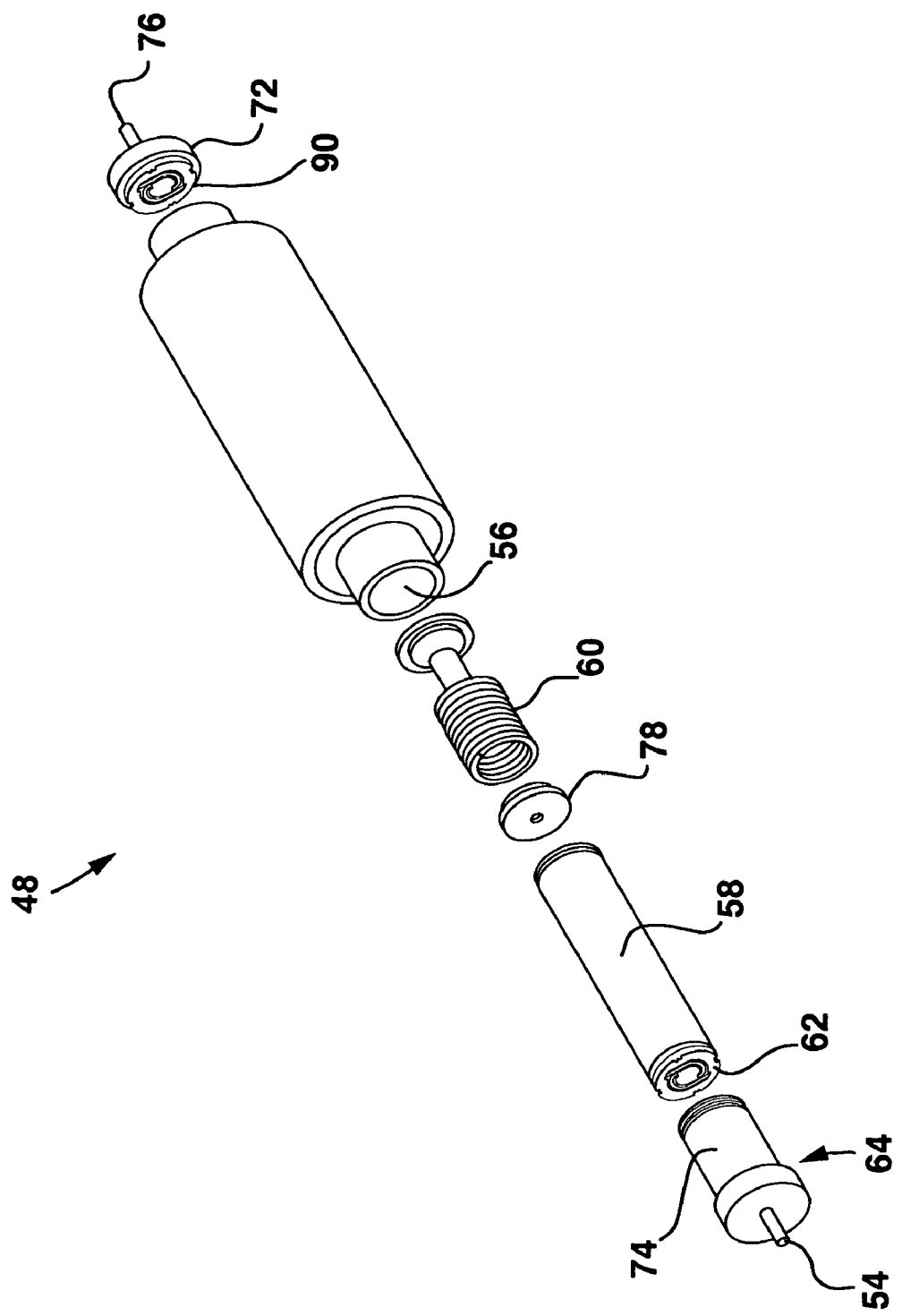
FIG. 8 shows an exploded view of the piston pump of FIG. 7 embodiment.
Figure 9:
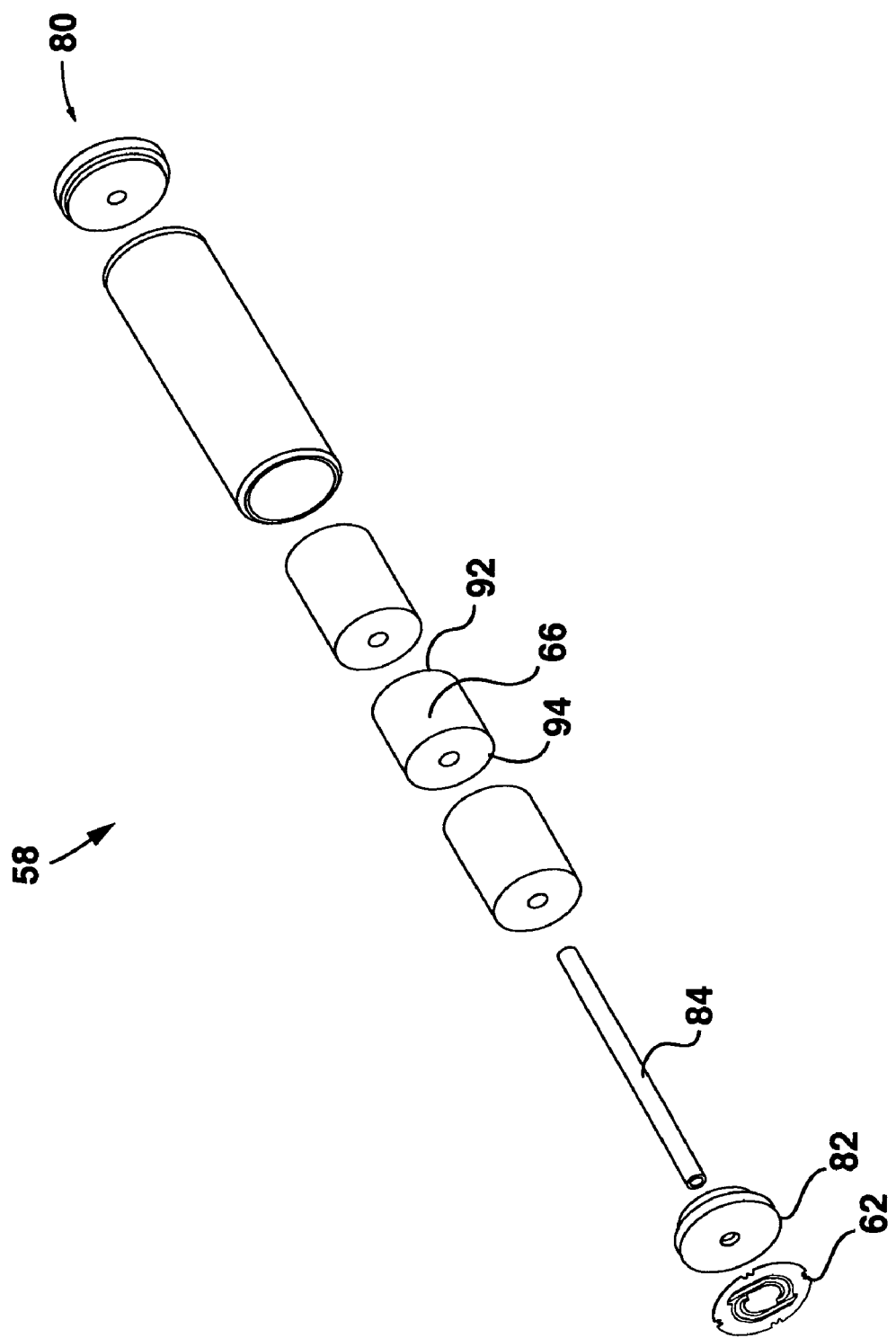
FIG. 9 shows an exploded view of a pump piston for a piston pump three-coil embodiment.
Figure 10:
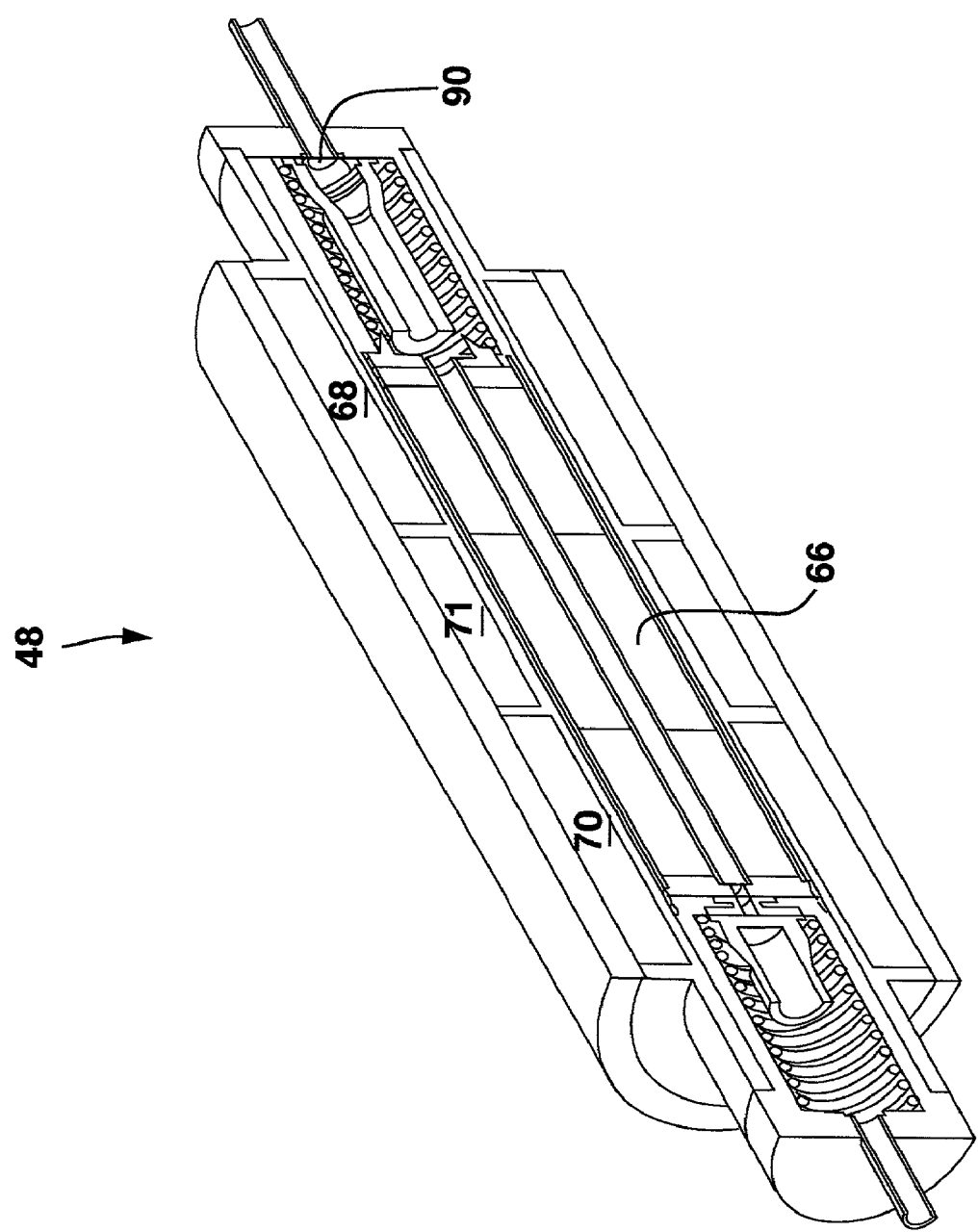
FIG. 10 shows an isometric cross-section view of a pump piston for a piston pump three-coil embodiment.
Figure 11:
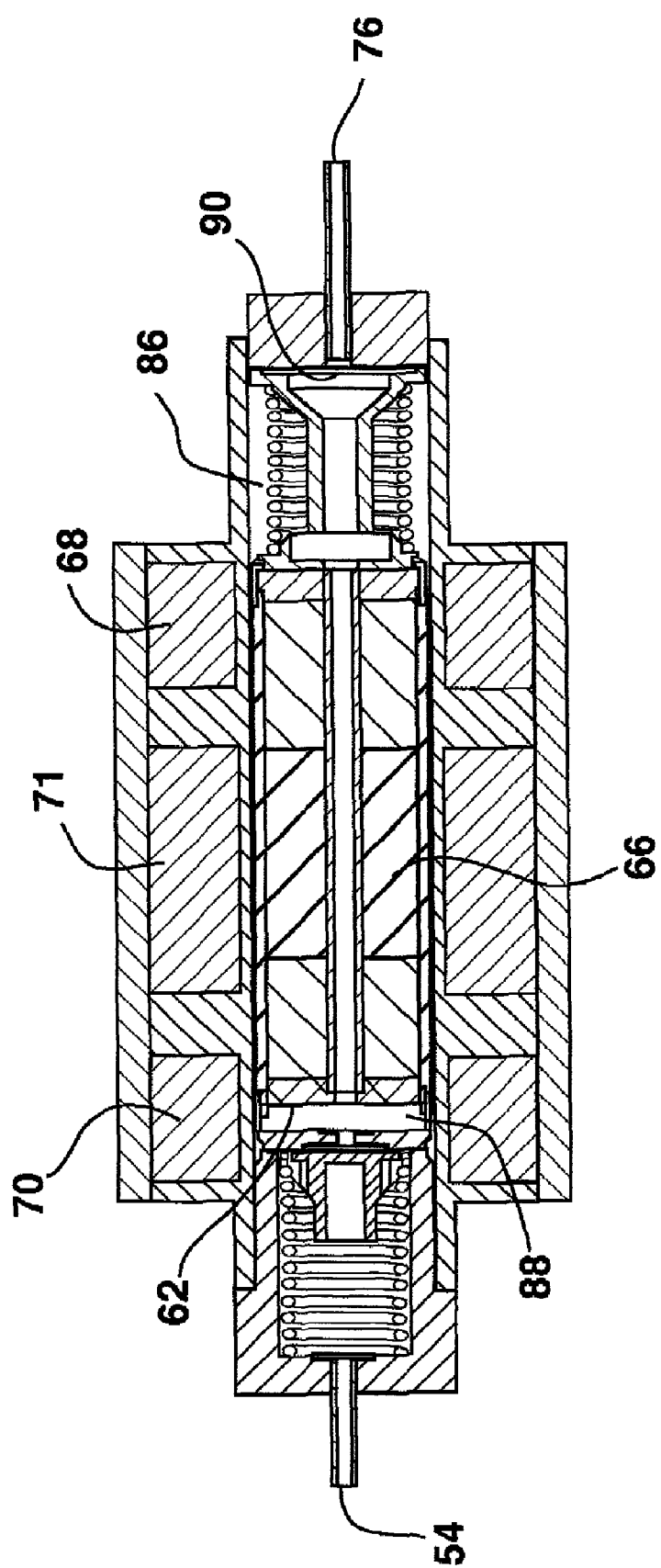
FIG. 11 shows a cross section view of a pump piston for a piston pump three-coil embodiment.
Figure 12A:
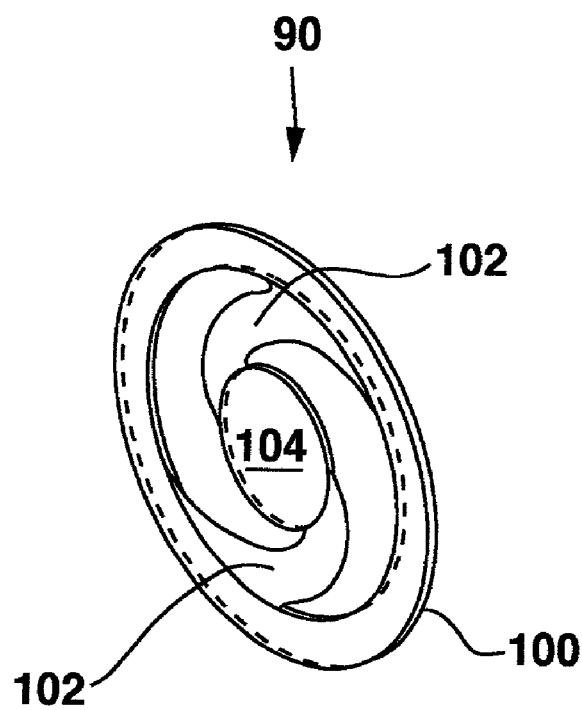
FIGS. 12a–12b show an anti-cavitation valve second embodiment.
Figure 12B:
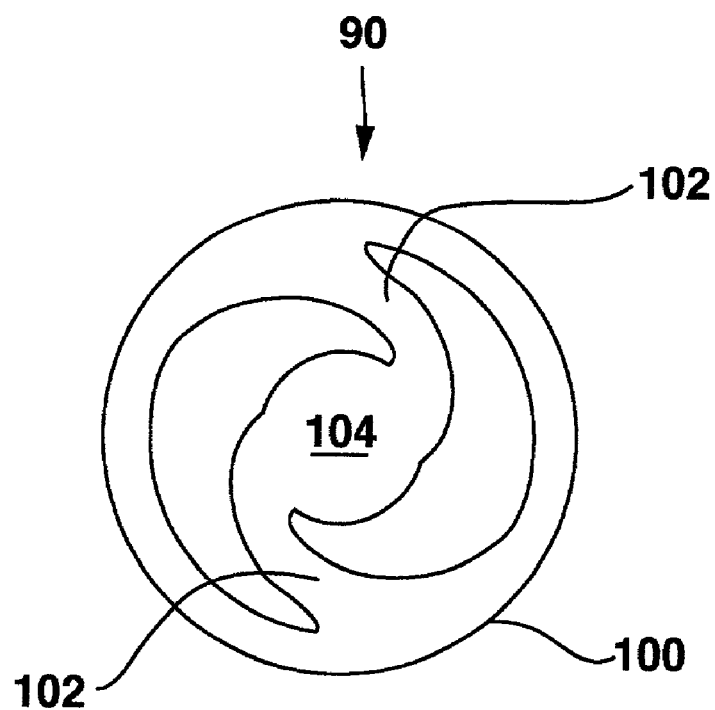
Figure 13A:
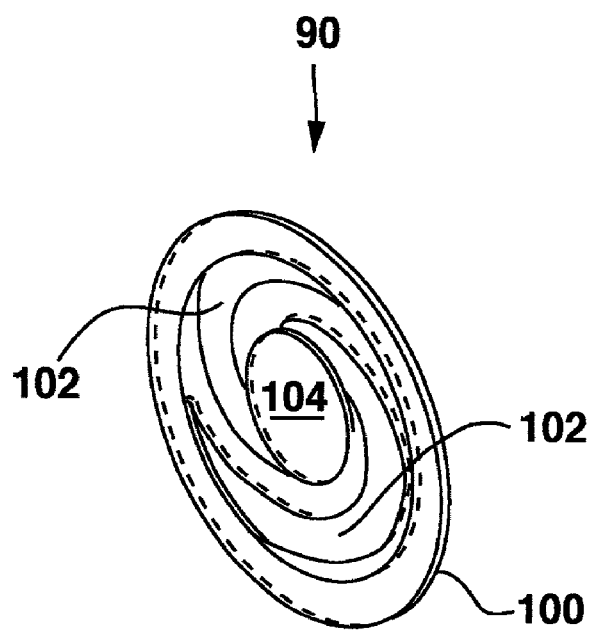
FIGS. 13a–13b show an anti-cavitation valve third embodiment.
Figure 13B:
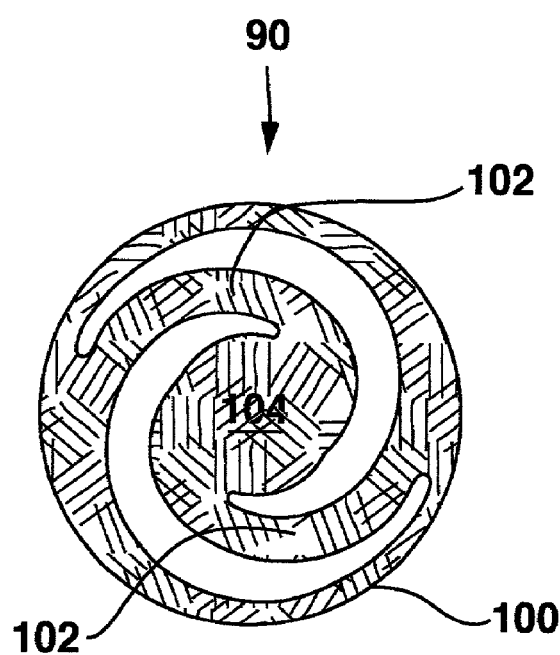
Figure 14A:
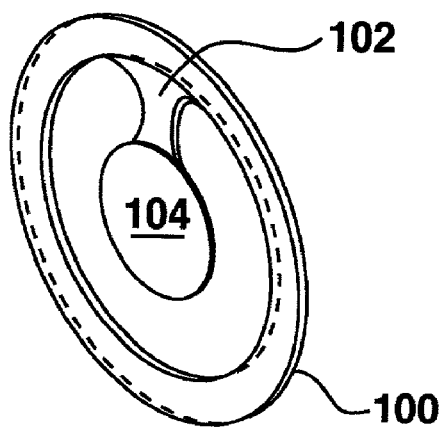
FIGS. 14a–14b show an anti-cavitation valve fourth embodiment.
Figure 14B:
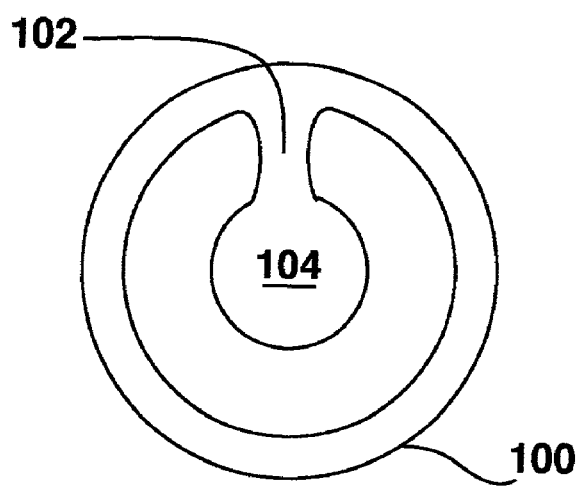
Figure 15:
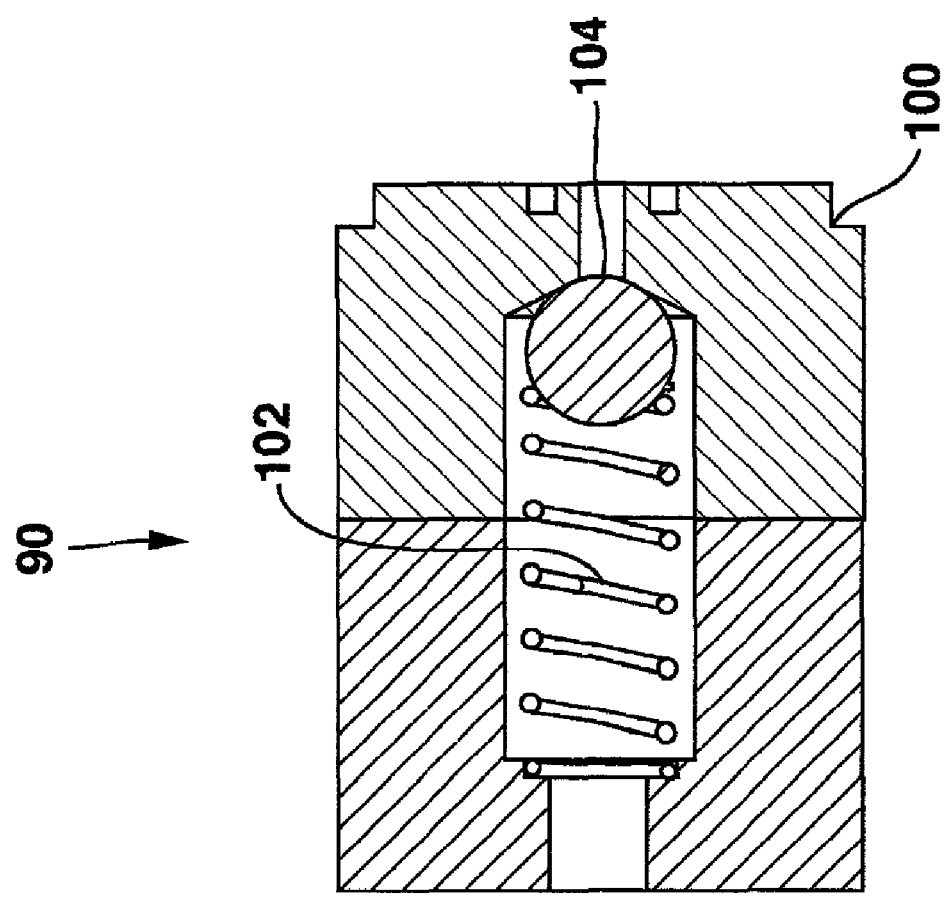
FIG. 15 shows an anti-cavitation valve fifth embodiment.

FIGS. 3–6 show views of therapeutic substance delivery device 30 embodiments. An implantable therapeutic substance delivery device 30 with a piston pump comprises a housing 41, a therapeutic substance reservoir 42, a power source 44, electronics 46, and a piston pump 48. Typically, the therapeutic substance delivery device 30 components are carried in a single housing 41, such as shown in FIGS. 3 and 4, that is manufactured from a material that is biocompatible and hermetically sealed such as titanium, tantalum, stainless steel, plastic, ceramic, and the like. Therapeutic substance delivery device 30 components can also be placed in more than one housing 41, such as shown in FIGS. 5 and 6, that are appropriately coupled. The therapeutic substance reservoir 42 can be placed inside the housing 41 or can be separated from the housing 41 with a fluid coupling such as a tube between the reservoir 41 and the housing 41. The therapeutic substance reservoir 42 is configured to contain a therapeutic substance 36 and may use geometries such as a metal bellows, polyomeric bag, and the like. The therapeutic substance reservoir 42 has a reservoir outlet 52 and can have a septum 40 for refilling the reservoir 42.

The power source 44 is carried in the housing 41. The power source 44 is selected to operate the piston pump 48 and electronics 46 such as a lithium ion (Li+) battery, capacitor, and the like. The electronics 46 are coupled to the power source 44 and typically include memory and a controller. The controller can be an Application Specific Integrated Circuit (ASIC) state machine, a gate array, or may include a microprocessor. The electronics 46 are configured to control the piston pump 48 infusion rate and can be configured to operate many other features such as patient alarms and the like. The electronics 46 can also include telemetry circuitry configured to receive and send information when the therapeutic substance delivery device 30 is implanted to allow programming of the infusion rate. The piston pump 48 is coupled to the electronics 46 and coupled to the therapeutic substance reservoir outlet 52 and configured for pumping therapeutic substance 36 from the therapeutic substance reservoir 42 through an infusion outlet 54 at a programmed rate.

FIGS. 7–11 show a three-coil embodiment of the piston pump. The piston pump 48 comprises a pump cylinder 56, a pump piston 58, a biasing element 60, an inlet valve 62, an outlet valve 64, a permanent magnet 66, a first coil 68, and a second coil 70. The piston pump 48 is coupled to the electronics 46, the therapeutic substance reservoir outlet 52, and the infusion outlet 54. The piston pump 48 is configured for pumping therapeutic substance 36 from the reservoir 42 through an infusion outlet 54 at a programmed rate.

The pump cylinder 56 has an inlet enclosure 72, an outlet enclosure 74, a therapeutic substance inlet 76, and an infusion outlet 54. The inlet enclosure 72 transitions the pump cylinder 56 to the therapeutic substance inlet 76. The outlet enclosure 74 transitions the pump cylinder 56 to the infusion outlet 54. The therapeutic substance inlet 76 is coupled to a therapeutic substance reservoir outlet 52 and coupled to the inlet enclosure 72 on the pump cylinder 56. Some embodiments can include a piston seal 78 positioned between the pump cylinder 56 and the pump piston 58 to reduce therapeutic substance 36 flow between the pump piston 58 and the pump cylinder 56 and provide other functions. The piston seal 78 can be configured to serve as a guide for the biasing element 60 and to cushion the pump piston 58 at the end of pump piston 58 retraction for the intake stroke. The piston seal 78 is manufactured from a resilient material with good sealing qualities such as synthetic rubber, PTFE, silicone, and the like.

The pump piston 58 is moveable within the pump cylinder 56 and has a piston inlet end 80, a piston outlet end 82, and a piston fluid path 84. The pump piston 58 forms an inlet chamber 86 between the pump piston 58 and the inlet enclosure 72 and a pumping chamber 88 between the pump piston 58 and the outlet enclosure 74. The inlet chamber 86 contains the therapeutic substance 36 that is displaced when the pump piston 58 retracts. The pumping chamber 88 contains the therapeutic substance 36 that is displaced when the pump piston 58 is actuated. The piston fluid path 84 is configured to provide fluid communication between the inlet chamber 86 and the pumping chamber 88 that is controlled by the inlet valve 62. The piston fluid path 84 can take a wide variety of forms such as a central fluid path, a side fluid path, a partial central and partial side fluid path, and the like.

The biasing element 60 is positioned in the pump cylinder inlet chamber 86 between the pump piston 58 and the inlet enclosure 72. The biasing element 60 exerts force on the pump piston 58 to expulse therapeutic substance 36 through the infusion outlet 54. In some embodiments, the biasing element 60 exerts substantially the sole force on the pump piston 58 to expulse therapeutic substance 36 through the infusion outlet 54. The biasing element 60 also provides force to maintain the pump piston 58 in an actuated position until retracted to seal the inlet valve 62 against the outlet enclosure 74 to provide redundant protection against unintended flow of therapeutic substance 36 to the patient 38. The biasing element 60 can be one or more of a wide variety of biasing structures that are selected to provide the desired biasing force on the pump piston 58. The desired force of the biasing element 60 in a particular embodiment is the force required to overcome any frictional losses during the pump piston 58 expulsion stroke, to generate pressure to open the outlet valve 64, and to overcome pressure losses between the infusion outlet 54 and the infusion site 34 that can be located at the distal end of the catheter 32. Some specific embodiments of the biasing element 60 include a spring, a coil spring, and the like.

The inlet valve 62 is carried on the pump piston outlet end 82. The inlet valve 62 can be a variety of inlet valves 62 such as a flapper valve, annular flapper valve, ball valve, reed valve, duckbill valve, poppet valve, and the like. The outlet valve 64 is carried in the outlet enclosure 74 and coupled to the infusion outlet 54. The outlet valve 64 improves piston pump 48 safety by substantially preventing unintended flow of therapeutic substance 36 when the reservoir 42 pressure is greater than the infusion site 34 pressure. The outlet valve 64 improves piston pump 48 accuracy by maintaining sufficient back pressure to keep the inlet valve 62 closed during therapeutic substance 36 expulsion through the infusion outlet 54 so that addition therapeutic substance 36 is not infused when the reservoir 42 pressure is greater than the infusion site 34 pressure. The outlet valve 64 can be a variety of outlet valves 64 such as a flapper valve, ball valve, reed valve, duckbill valve, poppet valve, and the like.

The anti-cavitation valve 90 is positioned in fluid communication with the therapeutic substance inlet 76. The anti-cavitation valve 90 substantially prevents therapeutic substance 36 in the inlet chamber 86 from flowing back through the therapeutic substance inlet 76 during pump piston 58 retraction. Since the therapeutic substance 36 cannot flow backwards, pressure in the inlet chamber 86 increases as the pump piston 58 retracts causing the therapeutic substance 36 to flow through the piston fluid path 84 without causing the pump chamber 88 pressure to drop low enough to cause dissolved gasses to come out of solution. Also by substantially preventing the back flow of therapeutic substance 36 through the therapeutic substance inlet 76 during pump piston 58 retraction, piston pump 58 efficiency is improved because wasted therapeutic substance 36 flow is minimized. The anti-cavitation valve 90 can be a wide variety of anti-cavitation valves 90 such as a flapper valve, annual flapper valve, ball valve, reed valve, duckbill valve, poppet valve, and the like. The anti-cavitation valve is described in more detail under FIGS. 11–15. In addition to displacing therapeutic substance 36 that operates the inlet valve 62, outlet valve 64, and anti-cavitation valve 90, the pump piston 58 carries a permanent magnet 66.

The permanent magnet 66 is at least a first permanent magnet 66 having a first pole 92 and a second pole 94. The permanent magnet 66 is carried by the pump piston 58 and acted on by the magnetic fields created by the coils 67 that include at least the first coil 68 and at least the second coil 70. When the first coil 68 and second coil 70 are energized, the coils 67 produce an electromagnetic axial force that acts on the permanent magnet 66 to impart motion to the pump piston 58. In some embodiments, there can be more than one permanent magnet 66 such as a first permanent magnet 66, a second permanent magnet 96, a third permanent magnet 98 and so forth. Also in some embodiments, there can be more than a first coil 68 and second coil 70 such as a third coil 71 and so fourth. When using more than one permanent magnet 66, like poles are positioned adjacent to one another, and there are N−1 operational permanent magnets 66 where N is the number of coils 67 in the range from about 3 to 10. The permanent magnet 66 is manufactured from a hard ferromagnetic material such as samarium cobalt, neodymium, ceramic, alnico, and the like. Since the permanent magnet 66 material is typically not therapeutic substance compatible or biocompatible, the permanent magnet 66 is typically isolated from the therapeutic substance 36 by the piston fluid path 84 and the pump piston 58 sealed is by the piston inlet end 80 and piston outlet end 82. Positioned in operating relationship to the permanent magnet 66 are the first coil 68 and the second coil 70.

When the pump piston 58 is fully positioned toward the inlet enclosure 72, the maximum pump chamber 88 volume is created. The pump chamber 88 has a pump chamber 88 volume comprising a stroke volume and a dead volume. The stroke volume is in the range from about 0.5 micro liters to about 5.0 micro liters. The sum of an inlet valve 62 opening pressure and the outlet valve 64 opening pressure exceeds the maximum pressure of the reservoir 42 less the infusion site 34 pressure to substantially prevent free flow of therapeutic substance 36 to the patient 38. The dead volume is less than half the stroke volume in the range from about 0.25 micro liters to about 2.5 micro liters. The piston pump's 48 small dead volume compared to the stroke volume improves the piston pump's 48 capability to pass air because of the low vacuum pressure that is typically generated in the pump chamber 88. The inlet valve 62 and outlet valve 64 opening pressures are selected to prevent unintended infusion under extreme operating conditions. Unintended infusion is substantially prevented by selecting the inlet valve 62 opening pressure and the outlet valve 64 opening pressure so the sum of these pressures is greater than the maximum pressure difference between the reservoir 42 and the infusion site 34. For example, unintended infusion is prevented when the reservoir 42 pressure is high and the ambient pressure (typically the same as the infusion site 34 pressure) is low that can occur when the reservoir 42 is full and the patient 38 is exposed to high temperature at high altitude.

The piston pump's 48 ability to pass air and operate accurately is a function of the piston pump's 48 compression ratio, the reservoir outlet 52 pressure, the infusion outlet 54 pressure, and outlet valve 64 cracking (opening) pressure. For adiabatic systems with ideal gases, the compression ratio in the pump chamber 88 can be expressed as $$CR_{pc} = \frac{V_{pc\ final}}{V_{pc\ initial}} \quad \text{(Equation 1)}$$

where $CR_{pc}$ is the compression ratio in the pump chamber 88, $V_{pc\ final}$ is the final volume in the pump chamber 88 calculated by (stroke volume+pump chamber dead volume) where stroke volume=piston area×piston stroke, and $V_{pc\ initial}$ is the initial volume in the pump chamber 88 also known as the pump chamber dead volume which is also the pump chamber volume remaining after the pump piston 58 has expulsed the stroke volume. The compression ratio in the inlet chamber 86 can be expressed as $$CR_{ic} = \frac{V_{ic\ final}}{V_{ic\ initial}} \quad \text{(Equation 2)}$$

where $CR_{ic}$ is the compression ratio in the inlet chamber 86 and $V_{ic}$ is the volume in the inlet chamber 86, $V_{ic\ final}$= (stroke volume+inlet chamber dead volume), and $V_{ic\ initial}$= (inlet chamber dead volume). From these relationships, it is apparent that pump chamber 88 pressure will be decreasing and inlet chamber 86 pressure will be increasing as the pump piston 58 retracts. For therapeutic substance 36 to flow into the pump chamber 88 when gas bubbles are present, the pressure in the pump chamber 88 during the pump piston 58 stroke must drop substantially below the inlet chamber 86 pressure. For therapeutic substance 36 to flow out of the pump chamber 88, the expulsion pressure must be greater than the infusion outlet 54 pressure. Therapeutic substance 36 flows through the outlet valve 64 when $P_{pc} \geq P_a + P_{ovc}$, where $P_{pc}$ is the pressure in the pump chamber 88, $P_a$ is the ambient pressure at the infusion outlet 54, and $P_{ovc}$ is outlet valve 64 cracking (opening) pressure. By selecting the appropriate outlet valve 64 cracking pressure the risk of unintentional infusion can be substantially eliminated.

FIGS. 11–15 show some a piston pump with an anti-cavitation valve 90 and a few of the many potential anti-cavitation valve 90 embodiments. The anti-cavitation valve 90 is placed in fluid communication with the reservoir outlet 52 and the inlet chamber 86. The anti-cavitation valve 90 can be carried on an inlet enclosure 72 that is in fluid communication with the inlet chamber 86 or the anti-cavitation valve 90 can be positioned at other locations upstream of the inlet chamber 86 such as at the therapeutic substance inlet 76, the reservoir outlet 52, and the like. The anti-cavitation valve 90 is configured to open when the therapeutic substance inlet 76 pressure exceeds the inlet chamber pressure 86 and close when the inlet chamber 86 pressure exceeds the therapeutic substance inlet 86 pressure. The anti-cavitation valve 90 serves as a means for anti-cavitation valuing configured to substantially prevent retrograde or reverse flow of therapeutic substance 36 from the inlet chamber 86 back through the reservoir outlet 52.

By substantially preventing the retrograde flow of therapeutic substance 36, the anti-cavitation valve 90 contributes to the piston pump's 48 reduced pumping chamber 88 gas formation, improved efficiency, increased accuracy, and a many other improvements. The piston pump's 48 reduced pumping chamber 88 gas formation is achieved by the anti-cavitation valve 90 substantially preventing pumping chamber 88 pressures from dropping below a predetermined pressure to substantially prevent gases coming out of the therapeutic substance 36 solution to form air bubbles. The anti-cavitation valve 90 substantially prevents the formation of air bubbles by causing the pumping chamber 88 to fill rapidly and more completely when the pump piston 58 is retracted. The pumping chamber 88 fills more rapidly and completely because the anti-cavitation valve 90 substantially prevent retrograde flow of therapeutic substance 36 out of the inlet chamber 86 through the therapeutic substance inlet 76 during pump piston 58 retraction. Since the therapeutic substance 3 in the inlet chamber 86 cannot retrograde, the inlet chamber 86 contents are rapidly and substantially completely transferred to the pumping chamber 88. When the pumping chamber 88 fills rapidly pumping chamber 88 pressure is substantially prevented from decreasing below a predetermined low pumping chamber 88 pressure during pump piston 58 retraction. The therapeutic substance 36 contained in the pumping chamber 88 at or above the predetermined low pumping chamber 88 pressure retains dissolved gasses in the therapeutic substance 36. Piston pump 48 efficiency is improved because substantially all the therapeutic substance 36 that enters the inlet chamber 86 is transferred to the pumping chamber 88 for infusion. Piston pump 48 delivery accuracy is increased because few if any gas bubbles form in the pumping chamber 88 because pumping chamber 88 pressures do not go below the predetermined pressure.

The anti-cavitation valve 90 embodiments shown in FIGS. 12a–15 comprises a valve body 100, a valve spring 102, and a valve surface 104. For the anti-cavitation embodiments in FIGS. 12a–14b, the valve spring 102 and valve surface 104 are substantially coplanar when the valve spring 102 is not under load in an un-flexed position. This anti-cavitation valve 90 embodiment can be configured with a low opening pressure of less than about 6895 pascals for rapid operation. Wide varieties of anti-cavitation valve 90 configurations are possible such as a flapper valve, a metal foil flapper valve, ball and spring valve, piston and spring valve, reed valve, a duckbill valve, a poppet valve, and the like.

Figure 16:
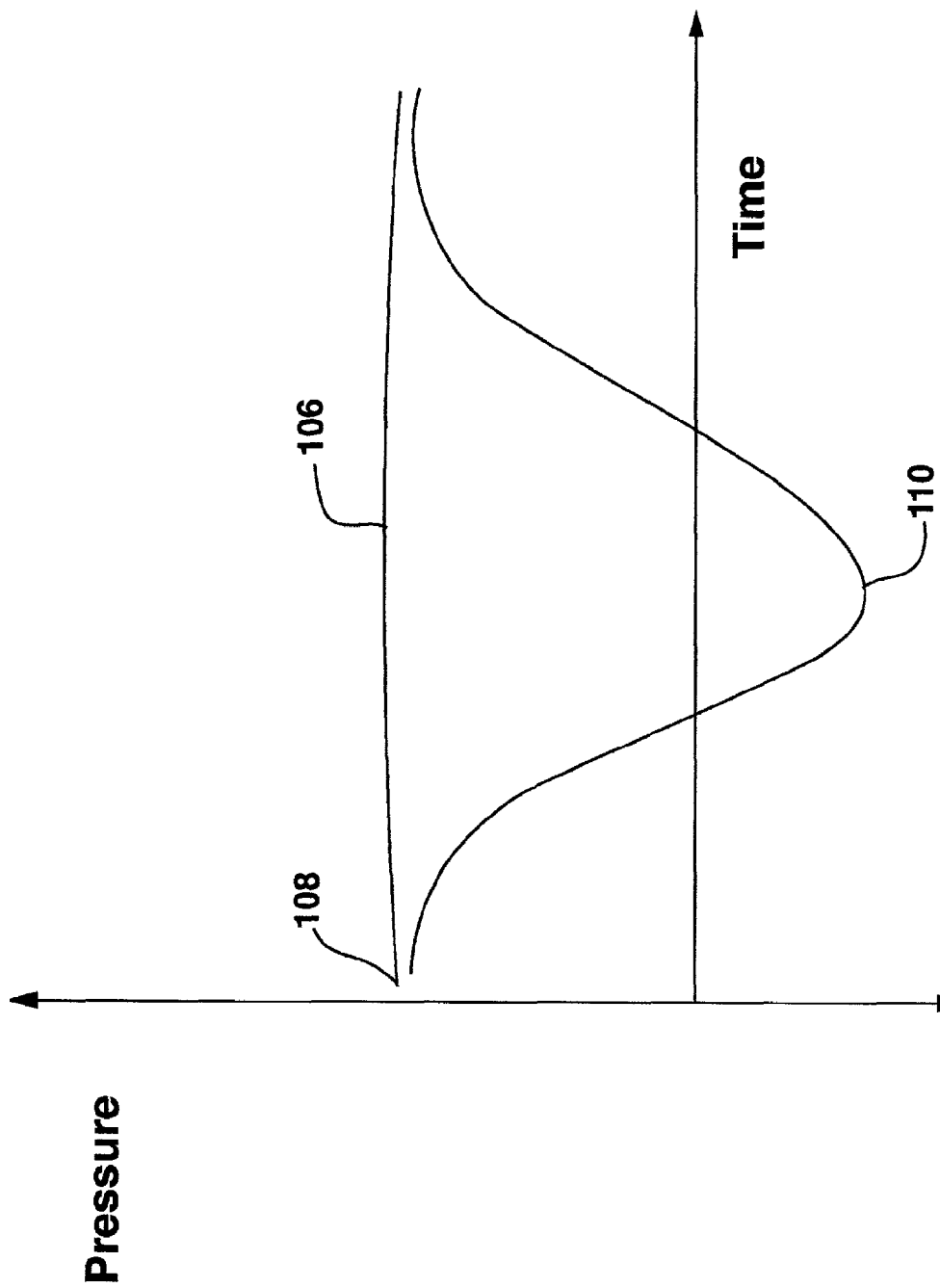
FIG. 16 shows a prophetic graph of pressures during pump piston retraction without an anti-cavitation valve.
Figure 17:
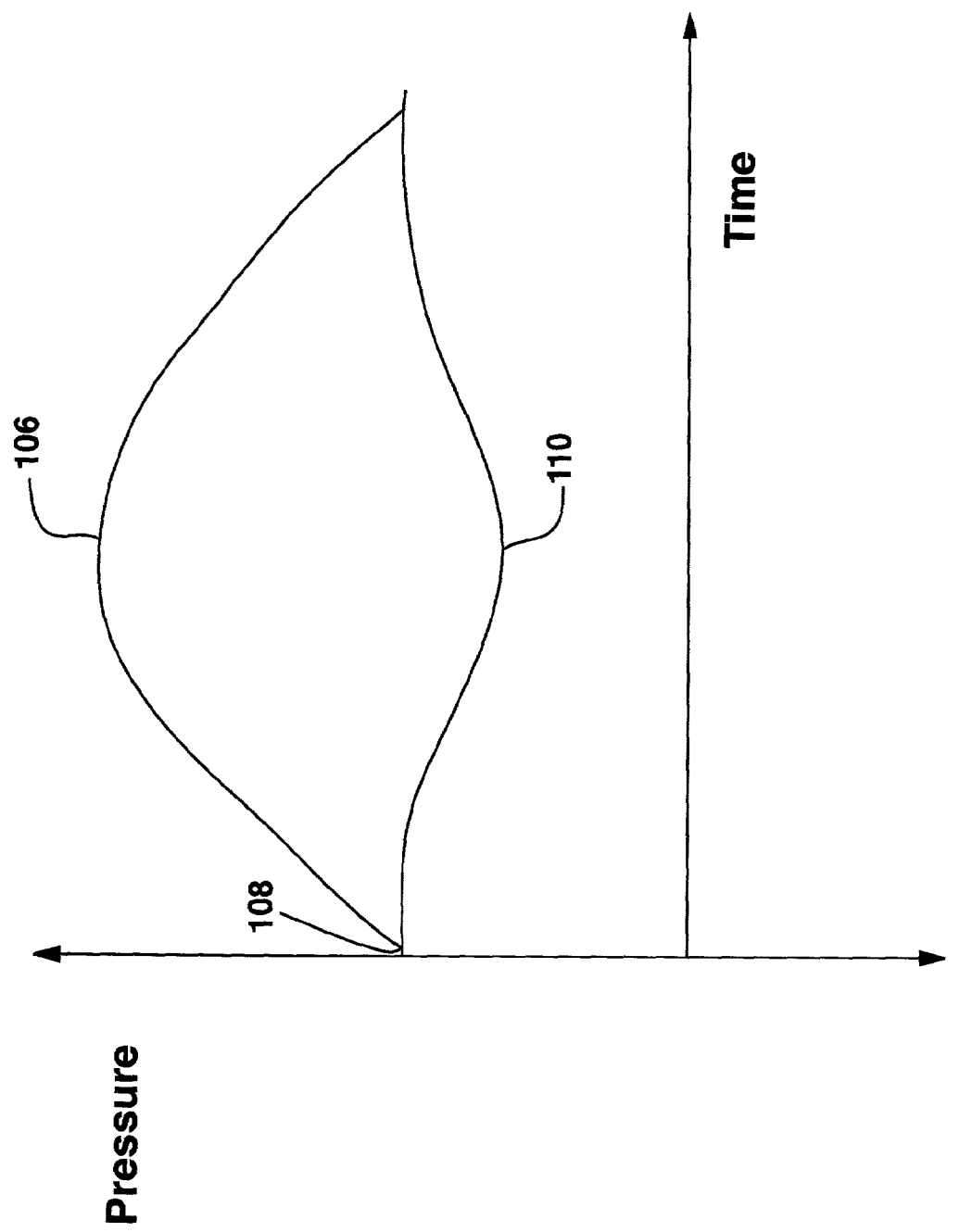
FIG. 17 shows a prophetic graph of pressures during pump piston retraction with an anti-cavitation valve embodiment.

FIGS. 16 and 17 show prophetic graph comparisons of pressures during pump piston 58 retraction without anti-cavitation valve 90 (FIG. 16) and with an anti-cavitation valve 90 (FIG. 17). The graphs, FIGS. 16 and 17, were drawn based upon how the implantable therapeutic substance delivery device 30 without and with an anti-cavitation valve 90 is believed to operation without developing empirical data to support the graphs. Without an anti-cavitation valve 90 (FIG. 16) during pump piston 58 retraction, inlet chamber pressure 106 would be expected to stay near the therapeutic substance inlet pressure 108 because there is fluid communication between the inlet chamber 86 and the therapeutic substance inlet 76 which is fluidly connected to the therapeutic substance reservoir 42. Pumping chamber pressure 110 would be expected to drop significantly because a pressure differential is necessary to fill the pumping chamber 88. With an anti-cavitation valve 90 (FIG. 17) during pump piston 58 retraction, inlet chamber pressure 106 would be expected to increase because of the substantially incompressible nature of the therapeutic substance 36 in the inlet chamber 86 that is prevented from retrograde movement due to the anti-cavitation valve 90. Pumping chamber pressure 110 would be expected to decrease only a small amount because the required pressure differential for therapeutic substance 36 flow would be achieved. The pumping chamber pressure 110 decrease would not typically be low enough to cause gases to come out of solution because the inlet chamber pressure 106 would rapidly fill the pumping chamber 88 with therapeutic substance 36.

Operation

FIGS. 1–11 show a variety of views that can assist in understanding operation of the implantable therapeutic substance delivery device 30 embodiment. Generally, therapeutic substance delivery device 30 embodiments begin operation by having electronics 46 programmed to operate the permanent piston pump 48 to deliver therapeutic substance 36 at a programmed rate. The therapeutic substance 36 is supplied from a therapeutic substance reservoir 42 to a therapeutic substance inlet 76. The piston pump 48 generally operates by retracting a pump piston 58 and then actuating the pump piston 58 while operating valves to deliver therapeutic substance 36 through an infusion outlet 54 at a programmed rate. This operation is repeated a predetermined number of times at predetermined intervals to delivery therapeutic substance 36 at the programmed rate. For example, a piston pump 48 with a stroke volume of 2.0 micro liters would typically be operated from a maximum of about 10 cycles per second (Hz) to achieve an infusion rate of 1.2 milliliters per minute to a minimum of about 1.0 cycle per hour to achieve an infusion rate of about 48 micro liters per day.

Retracting the pump piston 58 is initiated when a first coil 68 for current flow in a first direction is energized and a second coil 70 for current flow in an opposite direction are energized to create a electromagnetic axial force. The pump piston 58 is retracted when the electromagnetic axial forces acts on a permanent magnet 66 carried on the pump piston 58. While the pump piston 58 is retracting, an inlet valve 62 is opened, an anti-cavitation valve 90 is closed, and a biasing element 60 is loaded. A pump chamber 88 is filled with therapeutic substance 36 through the inlet valve 62 while the pump piston 58 is being retracted. The anti-cavitation valve 90 prevents therapeutic substance 36 in the inlet chamber 86 from flowing back to the therapeutic substance reservoir 42 when the pump piston 58 retracts. The anti-cavitation valve 90 helps maintain higher pump chamber 88 pressures during pump piston 58 retraction, which makes it easier to pass air bubbles. In an embodiment having a piston seal 78, during pump piston 58 retraction the piston seal 78 can also be configured to dampen the shock when the pump piston 58 reaches its fully retracted position. By dampening this shock, the piston seal 78 can reduce some wear and noise that occurs when the pump piston 58 reaches its fully retracted position.

During pump piston 58 retraction both the inlet chamber 86 and pump chamber 88 are filled with therapeutic substance 36, the pressure in the inlet chamber 86 will increase rapidly due to the incompressibility of liquids which will cause the therapeutic substance 36 to flow through the piston fluid path 84 into the pump chamber 88 without causing the pump chamber 88 pressure to decrease to the level that would cause gasses to come out of solution. After the pump piston 58 is retracted, operation of the piston pump 48 continues when the pump piston 58 is actuated.

Actuating the pump piston is initiated when the first coil 68 for current flow in the first direction is de-energized, and the second coil 70 for current flow in the opposite direction is de-energized to collapse the electromagnetic axial force. As the electromagnetic axial force collapses, the biasing element 60 is unloaded, and the pump piston 58 is actuated by the biasing element 60 driving the pump piston 58 toward the outlet enclosure 74. While the pump piston 58 is being actuated, pressure generated in the pumping chamber 88 opens the outlet valve 64. The open outlet valve 64 permits a stroke volume to be expulsed through the infusion outlet 54 while the pump piston 58 is actuated. The anti-cavitation valve 90 opens to permit therapeutic substance 36 to flow from the therapeutic substance inlet 76 into the inlet chamber 86. The therapeutic substance 36 discharged through the infusion outlet 54 is delivered at a programmed rate. In some embodiments during pump piston actuation, the piston seal 78 substantially prevents therapeutic substance 36 from flowing around the pump piston 58 back into the inlet chamber 86. The previously discussed method embodiment elements are presented in a general sequence that is intended to be limiting only when a particular element is required to be sequence in a certain way for the entire method embodiment to be practical. Pump piston actuation can be mathematically characterized.

During piston actuation to expulse therapeutic substance 36, when the pump chamber 88 volume is decreasing and the inlet chamber 86 volume is increasing the following relationships exist. The final pressure in the pump chamber 88 can be express as $$P_{pc\ final} = \frac{P_{pc\ initial}}{CR_{pc}} \quad \text{(Equation 3)}$$

where $P_{pc\ final}$ is the final pressure in the pump chamber 88, $P_{pc\ initial}$ is the initial pressure in the pump chamber 88, and $CR_{pc}$ is the compression ratio in the pump chamber 88. The final pressure in the inlet chamber 86 can be expressed as $$P_{ic\ final} = \frac{P_{ic\ initial}}{CR_{ic}} \quad \text{(Equation 4)}$$

where $P_{ic\ final}$ is the final pressure in the inlet chamber 86, $P_{ic\ initial}$ is the initial pressure in the inlet chamber 86, and $CR_{ic}$ is the compression ratio in the pump chamber 88. Therapeutic substance 36 flows through the outlet valve 64 when $P_{pc\ final} \geq P_a + P_{ovc}$ (Equation 5) where $P_{ic}$ is the initial pressure in the inlet chamber 86, $P_a$ is the ambient pressure at the pump outlet, and $P_{ovc}$ is outlet valve 64 cracking (opening) pressure. The above relationships assume there is no air in the pump chamber 88 and since liquids are essential incompressible $P_{ic}$ decreases as the pump piston 58 is actuated.

Figure 18:
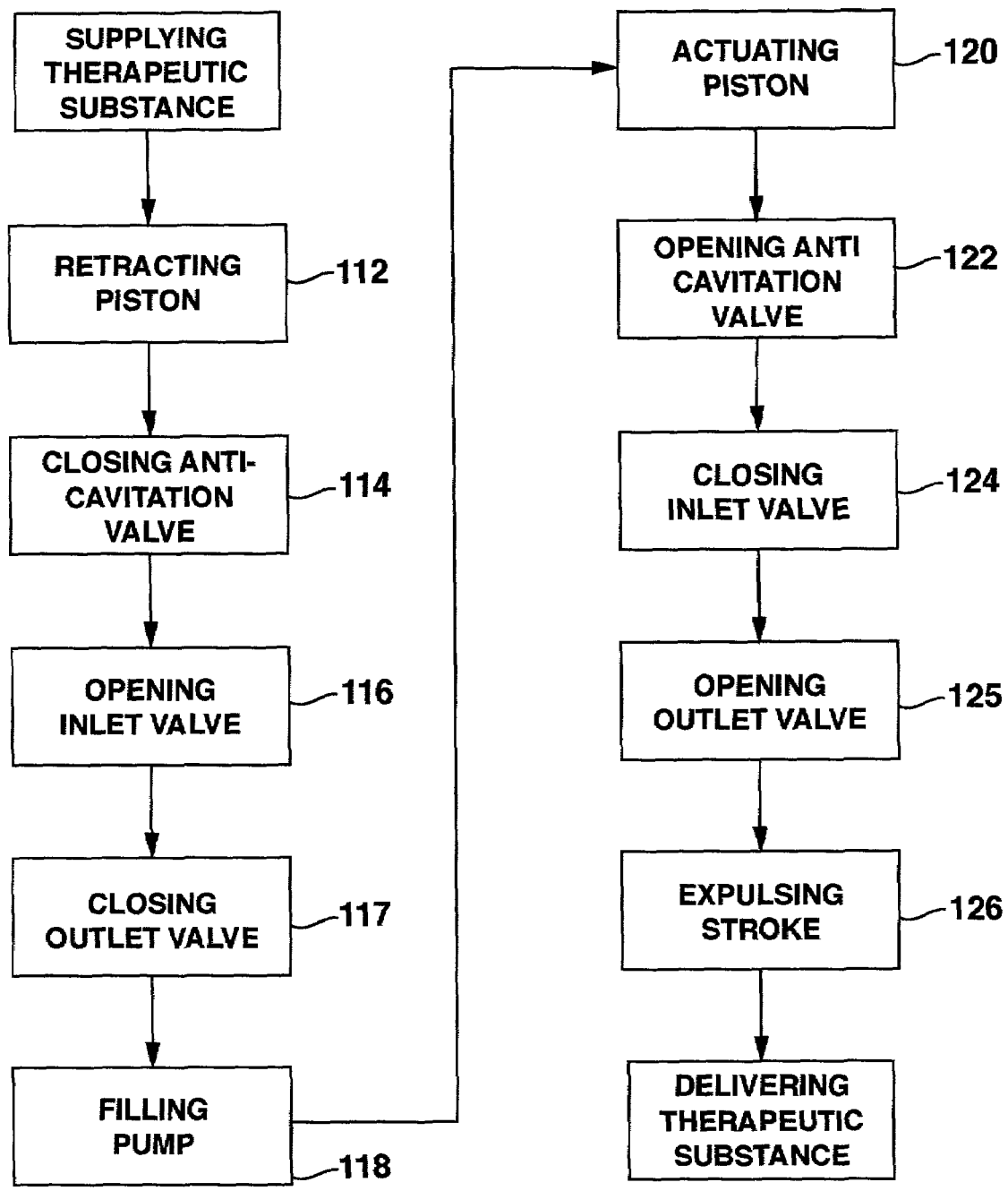
FIG. 18 shows a flow diagram of a method for controlling the flow of therapeutic substance into a piston pump with an anti-cavitation valve embodiment; and, FIG. 19 shows a flow diagram of a method for operating an anti-cavitation valve in a piston pump embodiment.

FIG. 18 shows a flow diagram of a method for controlling the flow of therapeutic substance into a piston pump 58 for an implantable therapeutic substance delivery device 30. The method begins with retracting 112 the pump piston 58 with an electromagnetic axial force acts on the pump piston 58. As the pump piston retracts 112, the inlet valve opens 116 to permit filling the pump chamber 88, the outlet valve closes 117, and the anti-cavitation valve closes 114. The anti-cavitation valve closes 114 when the pressure in the inlet chamber exceeds the pressure in the therapeutic substance inlet. The pump chamber 88 begins filling 112 with therapeutic substance 36 flowing from a reservoir 42 through the open inlet valve 62. Once the pumping chamber 88 is substantially filled with therapeutic substance 36, the pump piston 58 is actuated 114 by changing the electromagnetic axial force acting on the pump piston 58. The electromagnetic force can be substantially eliminated by de-energizing the coils 67, so a biasing element 60 can actuate 120 the pump piston 58 or the electromagnetic force can be reversed to actuate 120 the pump piston 58. Once the pump piston 58 begins actuation 120, the inlet valve closes 124, the outlet valve opens 125, and the anti-cavitation valve opens 122. The inlet valve closes 124 when the pressure in the pump chamber 88 exceeds the pressure in the inlet chamber 86. The anti-cavitation valve opens 122 when the pressure in the therapeutic substance inlet 76 exceeds the pressure in the inlet chamber 86. With the inlet valve closed 124 and the pump piston actuating 120, a stroke volume is expulsed 126 through an infusion outlet 54. Operation of the anti-cavitation valve 90 during pump piston retraction 112 prevents retrograde flow of therapeutic substance 36 from the inlet chamber 86 back through the therapeutic substance inlet 76. Preventing retrograde flow assists in rapidly increasing pressure in the inlet chamber 86 that due to the incompressibility of liquids causes therapeutic substance 36 to flow through the piston fluid path 84 into the pump chamber 88 without causing the pump chamber 88 pressure to decrease to the level that would cause gasses to come out of solution.

Figure 19:
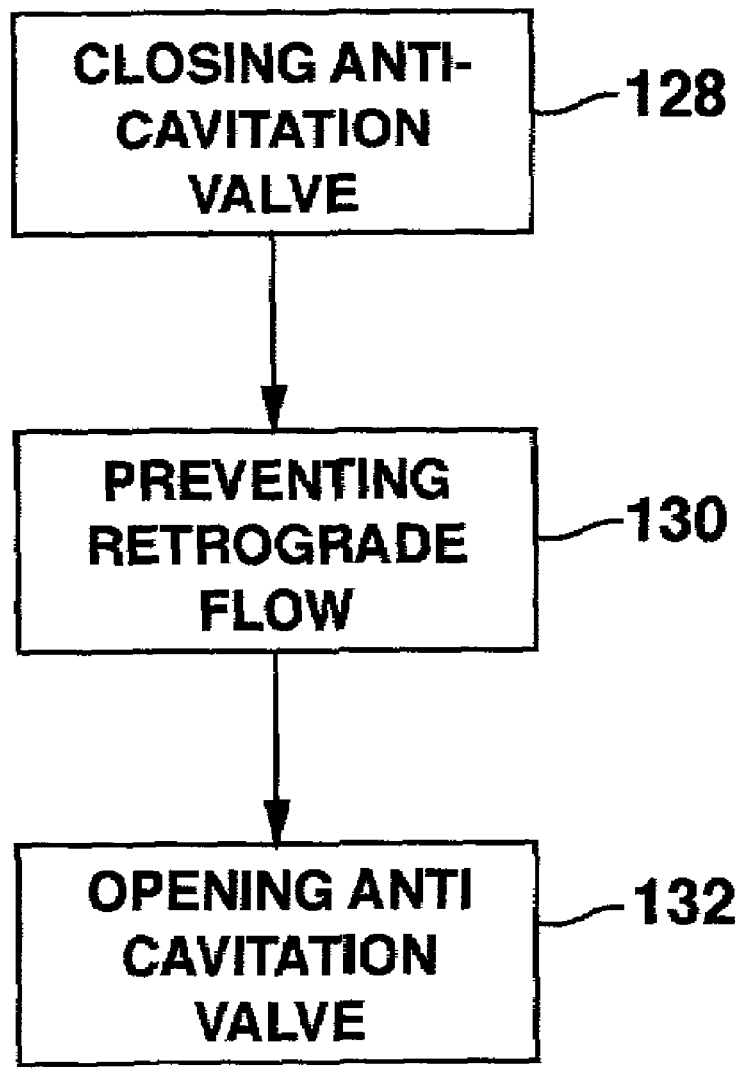

FIG. 19 shows a flow diagram for a method of operating an anti-cavitation valve 90 to substantially prevent retrograde flow of therapeutic substance 36 from a piston pump 48. The anti-cavitation valve is closed 128 when pressure in the inlet chamber 86 exceeds pressure in the therapeutic substance inlet 76. Pressure in the inlet chamber 86 exceeds the pressure in therapeutic substance inlet 76 when the pump piston 58 is retracted to fill the pumping chamber 88. Closing 128 the anti-cavitation valve substantially prevents retrograde flow of therapeutic substance 36 from the inlet chamber 86 through the therapeutic substance inlet 76. Preventing retrograde flow assists in rapidly increasing pressure in the inlet chamber 86 that due to the incompressibility of liquids causes therapeutic substance 36 to flow through the piston fluid path 84 into the pump chamber 88 without causing the pump chamber 88 pressure to decrease to the level that would cause gasses to come out of solution. When inlet chamber 86 pressure becomes lower that therapeutic substance inlet 76 pressure, the anti-cavitation valve is opened 132 to permit therapeutic substance 36 to flow into the inlet chamber 86.

Thus, embodiments of the anti-cavitation valve for a piston pump implantable therapeutic substance delivery device reduce gas formation, increase accuracy, improve efficiency, and have many other improvements. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable therapeutic substance delivery device comprising:
    a housing;
    a therapeutic substance reservoir carried in the housing, the therapeutic substance reservoir having a reservoir outlet;
    a power source carried in the housing;
    electronics coupled to the power source; and,
    a piston pump coupled to the electronics and coupled to the reservoir outlet, the piston pump comprising a pump cylinder in which a pump piston moves and an inlet chamber in fluid communication with a pumping chamber through a fluid path in the pump cylinder, wherein the piston pump is configured for pumping therapeutic substance from the therapeutic substance reservoir through an infusion port at a programmed rate;
    an inlet valve in fluid communication with the reservoir, the inlet valve configured for controlling therapeutic substance flow from the inlet chamber into the pumping chamber; and
    an anti-cavitation valve in fluid communication with the reservoir outlet and the inlet chamber, the anti-cavitation valve substantially preventing retrograde flow of therapeutic substance from the inlet chamber back toward the reservoir outlet.

2. The implantable therapeutic substance delivery device as in claim 1 wherein the anti-cavitation valve substantially prevents pumping chamber pressure from decreasing below a predetermined low pumping chamber pressure during pump piston retraction.

3. The implantable therapeutic substance delivery device as in claim 1 wherein the anti-cavitation valve causes a pumping chanter to fill more completely when the pump piston is retracted.

4. The implantable therapeutic substance delivery device as in claim 1 wherein the anti-cavitation valve improves piston pump efficiency by infusing substantially all the therapeutic substance that enters the inlet chamber.

5. The implantable therapeutic substance delivery device as in claim 1 wherein the anti-cavitation valve is carried on an inlet enclosure that is in fluid communication with the inlet chamber.

6. The implantable therapeutic substance delivery device as in claim 1 wherein the anti-cavitation valve is carried in the therapeutic substance inlet that is in fluid communication with the inlet chamber.

7. An implantable therapeutic substance delivery device comprising:
- at least one housing;
- a therapeutic substance reservoir carried in one of the at least one housing, the therapeutic substance reservoir having a reservoir outlet;
- a power source carried in one of the at least one housing;
- electronics coupled to the power source;
- a piston pump coupled to the electronics and coupled to the reservoir outlet, the piston pump comprising a pump cylinder in which a pump piston moves and an inlet chamber in fluid communication with a pumping chamber through a fluid path in the pump cylinder, wherein the piston pump is configured for pumping therapeutic substance from the therapeutic substance reservoir through an infusion port at a programmed rate;
- an inlet valve in fluid communication with the reservoir, the inlet valve configured for controlling therapeutic substance flow from the inlet chamber into the pumping chamber; and
- an anti-cavitation valve in fluid communication with the reservoir outlet and the inlet chamber, the anti-cavitation substantially preventing retrograde flow of therapeutic substance from the inlet chamber back toward the reservoir outlet.

8. The implantable therapeutic substance delivery device as in claim 7 wherein the anti-cavitation valve is carried on an inlet enclosure that is in fluid communication with the inlet chamber.

9. The implantable therapeutic substance delivery device as in claim 7 wherein the anti-cavitation valve is carded in the therapeutic substance inlet that is in fluid communication with the inlet chamber.

10. An implantable therapeutic substance delivery device comprising:
- at least one housing;
- a therapeutic substance reservoir carried in one of the at least one housing, the therapeutic substance reservoir having a reservoir outlet;
- a power source carried in one of the at least one housing;
- electronics coupled to the power source;
- means for pumping coupled to the electronics and coupled to the reservoir outlet, the means for pumping configured to pump a therapeutic substance from the therapeutic substance reservoir through an infusion outlet at a programmed rate;
- means for inlet valuing configured to control the flow of therapeutic substance from the reservoir outlet into a pumping chamber; and
- means for anti-cavitation valuing configured to substantially prevent retrograde flow of therapeutic substance from the inlet chamber back toward the reservoir outlet.

11. The implantable therapeutic substance delivery device as in claim 10 wherein the at least one housing comprises one housing.

12. The implantable therapeutic substance delivery device as in claim 10 wherein the means for anti-cavitation valving is carried on an inlet enclosure that is in fluid communication with the inlet chamber.

13. The implantable therapeutic substance delivery device as in claim 10 wherein the means for anti-cavitation valving is carried in the therapeutic substance inlet that is in fluid communication with the inlet chamber.

14. An implantable therapeutic substance delivery device comprising:
- a housing;
- a therapeutic substance reservoir carried in the housing, the therapeutic substance reservoir having a reservoir outlet;
- a power source carried in the housing;
- electronics coupled to the power source; and,
- a piston pump coupled to the electronics and coupled to the reservoir outlet, the piston pump comprising a pump cylinder in which a pump piston moves and an inlet chamber in fluid communication with a pumping chamber through a fluid path in the pump cylinder, wherein the piston pump is configured for pumping therapeutic substance from the therapeutic substance reservoir through an infusion port at a programmed rate;
- an inlet valve in fluid communication with the reservoir, the inlet valve configured for controlling therapeutic substance flow from the inlet chamber into the pumping chamber; and
- an anti-cavitation valve in fluid communication with the reservoir outlet and the inlet chamber, the anti-cavitation substantially preventing retrograde flow of therapeutic substance from the inlet chamber back toward the reservoir outlet;
- wherein the anti-cavitation valve substantially prevents pumping chamber pressure from decreasing below a predetermined low pumping chamber pressure during pump piston retraction such that the therapeutic substance contained in the pumping chamber at the predetermined low pumping chamber pressure retains dissolved gasses in the therapeutic substance.

15. The implantable therapeutic substance delivery device as in claim 14 wherein the anti-cavitation valve causes a pumping chamber to fill more completely when the pump piston is retracted.

16. The implantable therapeutic substance delivery device as in claim 14 wherein the anti-cavitation valve improves piston pump efficiency by infusing substantially all the therapeutic substance that enters the inlet chamber.

17. The implantable therapeutic substance delivery device as in claim 14 wherein the anti-cavitation valve is carried on an inlet enclosure that is in fluid communication with the inlet chamber.

18. The implantable therapeutic substance delivery device as in claim 14 wherein the anti-cavitation valve is carried in the reservoir outlet that is in fluid communication with the inlet chamber.

19. The implantable therapeutic substance delivery device as in claim 14 further comprising an outlet valve configured to control the flow of therapeutic substance from the pumping chamber into the infusion port.

20. An implantable therapeutic substance delivery device comprising:
- a housing;
- a therapeutic substance reservoir carried in the housing, the therapeutic substance reservoir having a reservoir outlet;
- a power source carried in the housing;
- electronics coupled to the power source; and,
- a piston pump coupled to the electronics and coupled to the reservoir outlet, the piston pump comprising a pump cylinder in which a pump piston moves and an inlet chamber in fluid communication with a pumping chamber through a fluid path in the pump cylinder, wherein the piston pump is configured for pumping therapeutic substance from the therapeutic substance reservoir through an infusion port at a programmed rate;

an inlet valve in fluid communication with the reservoir, the inlet valve configured for controlling therapeutic substance flow from the inlet chamber into the pumping chamber; and an anti-cavitation valve in fluid communication with the reservoir outlet and the inlet chamber, the anti-cavitation substantially preventing retrograde flow of therapeutic substance from the inlet chamber back toward the reservoir outlet;

wherein the anti-cavitation valve substantially prevents pumping chamber pressure from decreasing below a predetermined low pumping chamber pressure during pump piston retraction and wherein the anti-cavitation valve increases piston pump delivery accuracy by substantially preventing the formation of gas bubbles in the pumping chamber.

21. The implantable therapeutic substance delivery device as in claim 20 wherein the anti-cavitation valve causes a pumping chamber to fill more completely when the pump piston is retracted.

22. The implantable therapeutic substance delivery device as in claim 20 wherein the anti-cavitation valve improves piston pump efficiency by infusing substantially all the therapeutic substance that enters the inlet chamber.

23. The implantable therapeutic substance delivery device as in claim 20 wherein the anti-cavitation valve is carried on an inlet enclosure that is in fluid communication with the inlet chamber.

24. The implantable therapeutic substance delivery device as in claim 20 wherein the anti-cavitation valve is carried in the reservoir outlet that is in fluid communication with the inlet chamber.

25. The implantable therapeutic substance delivery device as in claim 20 further comprising an outlet valve configured to control the flow of therapeutic substance from the pumping chamber into the infusion port.

26. An implantable therapeutic substance delivery device comprising:

at least one housing, wherein the at least one housing comprises a first housing coupled to a second housing;

a therapeutic substance reservoir carried in one of the at least one housing, the therapeutic substance reservoir having a reservoir outlet;

a power source carried in one of the at least one housing;

electronics coupled to the power source;

a piston pump coupled to the electronics and coupled to the reservoir outlet, the piston pump comprising a pump cylinder in which a pump piston moves and an inlet chamber in fluid communication with a pumping chamber through a fluid path in the pump cylinder, wherein the piston pump is configured for pumping therapeutic substance from the therapeutic substance reservoir through an infusion port at a programmed rate;

an inlet valve in fluid communication with the reservoir, the inlet valve configured for controlling therapeutic substance flow from the inlet chamber into the pumping chamber; and an anti-cavitation valve in fluid communication with the reservoir outlet and the inlet chamber, the anti-cavitation substantially preventing retrograde flow of therapeutic substance from the inlet chamber back toward the reservoir outlet.

27. The implantable therapeutic substance delivery device as in claim 26 wherein the therapeutic substance reservoir is carried in the first housing and the piston pump is carried in the second housing.

28. The implantable therapeutic substance delivery device as in claim 26 wherein the anti-cavitation valve is carried on an inlet enclosure that is in fluid communication with the inlet chamber.

29. The implantable therapeutic substance delivery device as in claim 26 wherein the anti-cavitation valve is carried in the reservoir outlet that is in fluid communication with the inlet chamber.

30. The implantable therapeutic substance delivery device as in claim 26 further comprising an outlet valve configured to control the flow of therapeutic substance from the pumping chamber into the infusion port.

31. An implantable therapeutic substance delivery device comprising:

at least one housing, wherein the at least one housing comprises a first housing coupled to a second housing;

a therapeutic substance reservoir carried in one of the at least one housing, the therapeutic substance reservoir having a reservoir outlet;

a power source carried in one of the at least one housing;

electronics coupled to the power source;

means for pumping coupled to the electronics and coupled to the reservoir outlet, the means for pumping configured to pump a therapeutic substance from the therapeutic substance reservoir through an infusion outlet at a programmed rate;

means for inlet valving configured to control the flow of therapeutic substance from the reservoir outlet into a pumping chamber; and means for anti-cavitation valving configured to substantially prevent retrograde flow of therapeutic substance from the inlet chamber back toward the reservoir outlet.

32. The implantable therapeutic substance delivery device as in claim 31 wherein the therapeutic substance reservoir is carried in the first housing and the means for pumping is carried in the second housing.

33. The implantable therapeutic substance delivery device as in claim 31 wherein the means for anti-cavitation valving is carried on an inlet enclosure that is in fluid communication with the inlet chamber.

34. The implantable therapeutic substance delivery device as in claim 31 wherein the means for anti-cavitation valving is carried in the reservoir outlet that is in fluid communication with the inlet chamber.

35. The implantable therapeutic substance delivery device as in claim 31 further comprising an outlet valve configured to control the flow of therapeutic substance from the pumping chamber into the infusion port.

36. An implantable therapeutic substance delivery device comprising:

a housing;

a therapeutic substance reservoir carried in the housing, the therapeutic substance reservoir having a reservoir outlet;

a power source carried in the housing;

electronics coupled to the power source; and, a piston pump coupled to the electronics and coupled to the reservoir outlet, the piston pump comprising a pump cylinder in which a pump piston moves and an inlet chamber in fluid communication with a pumping chamber through a fluid path in the pump cylinder, wherein the piston pump is configured for pumping therapeutic substance from the therapeutic substance reservoir through an infusion port at a programmed rate;

an inlet valve in fluid communication with the reservoir, the inlet valve configured for controlling therapeutic substance flow from the inlet chamber into the pumping chamber;

an anti-cavitation valve in fluid communication with the reservoir outlet and the inlet chamber, the anti-cavitation substantially preventing retrograde flow of therapeutic substance from the inlet chamber back toward the reservoir outlet; and an outlet valve configured to control the flow of therapeutic substance from the pumping chamber into the infusion port.

37. The implantable therapeutic substance delivery device as in claim 36 wherein the anti-cavitation valve causes a pumping chamber to fill more completely when the pump piston is retracted.

38. The implantable therapeutic substance delivery device as in claim 36 wherein the anti-cavitation valve improves piston pump efficiency by infusing substantially all the therapeutic substance that enters the inlet chamber.

39. The implantable therapeutic substance delivery device as in claim 36 wherein the anti-cavitation valve is carried on an inlet enclosure that is in fluid communication with the inlet chamber.

40. The implantable therapeutic substance delivery device as in claim 36 wherein the anti-cavitation valve is carried in the reservoir outlet that is in fluid communication with the inlet chamber.

41. An implantable therapeutic substance delivery device comprising:

at least one housing;

a therapeutic substance reservoir carried in one of the at least one housing, the therapeutic substance reservoir having a reservoir outlet;

a power source carried in one of the at least one housing; electronics coupled to the power source;

a piston pump coupled to the electronics and coupled to the reservoir outlet, the piston pump comprising a pump cylinder in which a pump piston moves and an inlet chamber in fluid communication with a pumping chamber through a fluid path in the pump cylinder, wherein the piston pump is configured for pumping therapeutic substance from the therapeutic substance reservoir through an infusion port at a programmed rate;

an inlet valve in fluid communication with the reservoir, the inlet valve configured for controlling therapeutic substance flow from the inlet chamber into the pumping chamber;

an anti-cavitation valve in fluid communication with the reservoir outlet and the inlet chamber, the anti-cavitation substantially preventing retrograde flow of therapeutic substance from the inlet chamber back toward the reservoir outlet; and an outlet valve configured to control the flow of therapeutic substance from the pumping chamber into the infusion port.

42. The implantable therapeutic substance delivery device as in claim 41 wherein the at least one housing comprises only one housing.

43. The implantable therapeutic substance delivery device as in claim 41 wherein the anti-cavitation valve is carried on an inlet enclosure that is in fluid communication with the inlet chamber.

44. The implantable therapeutic substance delivery device as in claim 41 wherein the anti-cavitation valve is carried in the reservoir outlet that is in fluid communication with the inlet chamber.

45. An implantable therapeutic substance delivery device comprising:

at least one housing;

a therapeutic substance reservoir carried in one of the at least one housing, the therapeutic substance reservoir having a reservoir outlet;

a power source carried in one of the at least one housing; electronics coupled to the power source;

means for pumping coupled to the electronics and coupled to the reservoir outlet, the means for pumping configured to pump a therapeutic substance from the therapeutic substance reservoir through an infusion outlet at a programmed rate;

means for inlet valving configured to control the flow of therapeutic substance from the reservoir outlet into a pumping chamber; and means for anti-cavitation valving configured to substantially prevent retrograde flow of therapeutic substance from the inlet chamber back toward the reservoir outlet;

an outlet valve configured to control the flow of therapeutic substance from the pumping chamber into the infusion port.

46. The implantable therapeutic substance delivery device as in claim 45 wherein the at least one housing comprises only one housing.

47. The implantable therapeutic substance delivery device as in claim 45 wherein the means for anti-cavitation valving is carried on an inlet enclosure that is in fluid communication with the inlet chamber.

48. The implantable therapeutic substance delivery device as in claim 45 wherein the means for anti-cavitation valving is carried in the reservoir outlet that is in fluid communication with the inlet chamber.

* * * * *

UNITED STATES PATENT AND TRADEMARK OFFICE
CERTIFICATE OF CORRECTION

| | | |
|---|---|---|
| PATENT NO. | : 7,201,746 B2 | |
| APPLICATION NO. | : 09/952870 | |
| DATED | : April 10, 2007 | |
| INVENTOR(S) | : James M. Olsen | |

It is certified that error appears in the above-identified patent and that said Letters Patent is hereby corrected as shown below:

Col. 12, line 54, "pumping chanter" should read -- pumping chamber --.

Col. 13, line 33, "is carded" should read -- is carried --.

Col. 13, line 52, "valuing configured" should read -- valving configured --.

Signed and Sealed this

Seventh Day of August, 2007

JON W. DUDAS
*Director of the United States Patent and Trademark Office*